(12) United States Patent
La Thangue

(10) Patent No.: US 7,160,677 B1
(45) Date of Patent: Jan. 9, 2007

(54) TRANSCRIPTION FACTOR DP-1

(75) Inventor: Nicholas Barrie La Thangue, Abingdon (GB)

(73) Assignee: Topotarget UK Limited, Oxfordshire (GB)

( * ) Notice: Subject to any disclaimer, the term of this patent is extended or adjusted under 35 U.S.C. 154(b) by 0 days.

(21) Appl. No.: 09/645,572

(22) Filed: Aug. 25, 2000

Related U.S. Application Data

(63) Continuation of application No. 09/078,596, filed on May 14, 1998, now Pat. No. 6,150,116, which is a continuation of application No. 08/428,131, filed as application No. PCT/GB93/02227 on Oct. 29, 1993, now Pat. No. 5,863,757.

(30) Foreign Application Priority Data

Oct. 29, 1992 (GB) ................... 9222715.6
Aug. 5, 1993 (GB) ................... 9316206.3

(51) Int. Cl.
*C16Q 1/70* (2006.01)
(52) U.S. Cl. ................ 435/5; 435/6; 435/7.1; 436/501; 436/518
(58) Field of Classification Search ........... 435/4, 435/5, 7.1, 69.1, 320.1, 325, 70.1, 8; 536/23.1, 536/23.5, 24.31
See application file for complete search history.

(56) References Cited

FOREIGN PATENT DOCUMENTS

WO    WO 93/15227    8/1993

OTHER PUBLICATIONS

Cao et al, Nature (ENGLAND) Jan. 9, 1992, 355 (6356) p. 176-9, ISSN 0028-0836.*
Bowie et al (Science, 1990, 247:1306-1310).*
Burgess et al (J of Cell Bio. 111:2129-2138, 1990).*
Lazar et al (Molecular and Cellular Biology, 1988, 8:1247-1252).*
Darbinian et al., J Cell Physiol. 2001 Dec.;189(3):334-40.*
Gura (Science, 1997, 278:1041-1042).*
Jain (Sci. Am., 1994, 271:58-65).*
Curti (Crit. Rev. in Oncology/Hematology, 1993, 14:29-39).*
Hartwell et al (Science, 1997, 278:1064-1068).*
Benzene structure downloaded from en.wikipedia.org on Jan. 5, 2006).*
Naphalene downloaded from en.wikipedia.org on Jan. 5, 2006.*
Shivji et al., Mol. Cell. Biol. vol. 11 (3) 1991, 1686-1695.
Watson et al., Molecular Biology (1987), Fourth Edition, vol. 1, p. 313.
Crystal, R.G., Science 270: 404-410, 1995.
Miller et al., FASEB J. 9. 190-199, 1995.
Madeline et al., PNAS 83:6761-6765.
Bekkers et al., Biochemica et Biophysica Acta 1089: 345-351, 1991.
Zamanian et al., The EMBO Journal vol. 11 No. 7 pp. 2603-2610, 1992, "Adevnovirus E1a prevents the retinoblastoma gene product from repressing the activity of a cellular transcription factor".
Kaelin et al., Cell, vol. 70, 351-364, Jul. 24, 1992, "Expression Cloning of a cDNA Encoding a Retinoblastoma-Binding Protein withE1F-like Properties".
Girling et al., Nature vol. 362, pp. 83-87 Mar. 4, 1993, "A new component of the transcription factor DRTF1/E2F".
LaThangue et al., Current Biology 1993, vol. 3 No. 8, pp. 554-557,"Transcriptional Complexity".
Helin et al., Genes & Development 7i:1850-1861 1993, "Heterodimerization of the Transcription Factors E2F-1 and DP-1 Leads to Cooperative Trans-Activation".
Galfe, G. and Milstein, C. Preparation of Monoclonal Antibodies: Strategies and Procedures, Methods in Enzymology 73: 3-46 (1981).
Goding, James. Monoclonal Antibodies: Principles and Practice, 118-123 (1983).
AS, Promoter interaction of the E1A-inducible factor E2F and its potential role in the formation of a multi-component complex, EMBO J., Jul. 1987;6(7):2061-8, Abstract.
AS, The adenovirus-inducible factor stimulates transcription after specfic DNA binding, Mol Cell Biol., Feb. 1989;9(2):578-85, Abstract.
Thalmeier, Nuclear factor E2F mediates basic transcription and transactivation b E1a of the human MYC promoter, Genes Dev., Apr. 1989;3(4):527-36, Abstract.
Hiebert, E1A-dependent trans-activation of the human MYC promoter is media by the E2F factor, Proc. Natl Acad Sci, May 1989;86(10):3594-8, Abstract.
Babiss, The cellular transcription factor E2f requires viral E1A and E4 gene products for incrased DNA-binding activity and functions to stimulat adenovirus E2A gene expression, J Virol., Jun. 1989;63(6):2709-17, Abstract.
Bagchi, Phosphorylation-dependent activation of the adenovirus-inducible E2F transcription factor in a cell-free system, Proc Natl Acad Sci, Jun. 1989;86(12):4352-6, Abstract.

* cited by examiner

*Primary Examiner*—Misook Yu
(74) *Attorney, Agent, or Firm*—Nixon & Vanderhye P.C.

(57) ABSTRACT

The invention provides a polynucleotide in substantially isolated form which includes a contiguous sequence of nucleotides which is capable of selectively hybridizing to SEQ ID NO: 1 or the complement of SEQ ID NO: 1, and a polypeptide in substantially isolated form which includes: (a) the protein in SEQ ID NO: 2; or (b) an allelic variant or species homologue thereof; or (c) a protein at least 70% homologous to (a); or (d) a fragment of any one of (a) to (c) capable of forming a complex with the E2 F-1 protein or related family member; or (e) a fragment of any one of (a) to (c) of at least 15 amino acids.

14 Claims, 15 Drawing Sheets

-82 ———∿∿∿∿∿∿→ -50 E2A promoter

Fig.4(a).
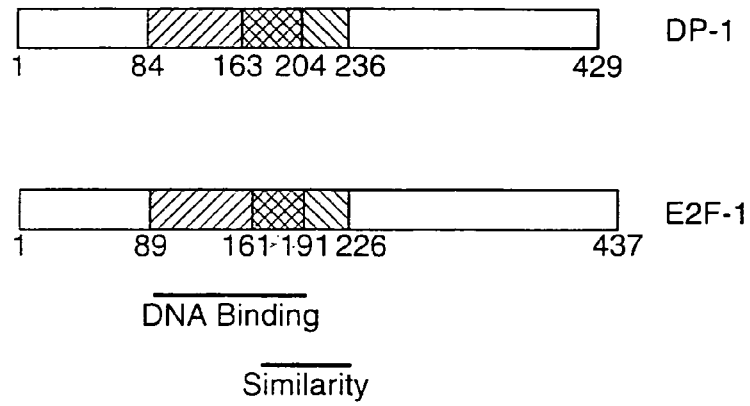
DNA Binding
Similarity
Fig.4(b).
```
       160                                                        200
DP-1   Y D Q K N I R R R V Y D A L N V L M A M N I I S K  E K K E  I K W I G L P T N S A Q
         | |||||| ||| ||||| | |  |  | |||  |  |
E2F-1  E V L K V Q K R R I Y D I T N V L E G I Q L I A K K S K N H I Q W L G S H T T V G V
       158                                                        199
       210                       240
       Q R R L E R I K Q K Q S Q L Q E L I L Q Q I A F K N L V Q R N
       ||| || |    ||||       |              ||
       G G R L E G L T Q D L R Q L Q E S E Q Q L D H L M N I C T T Q
       200                       230
```
Fig.4(c).
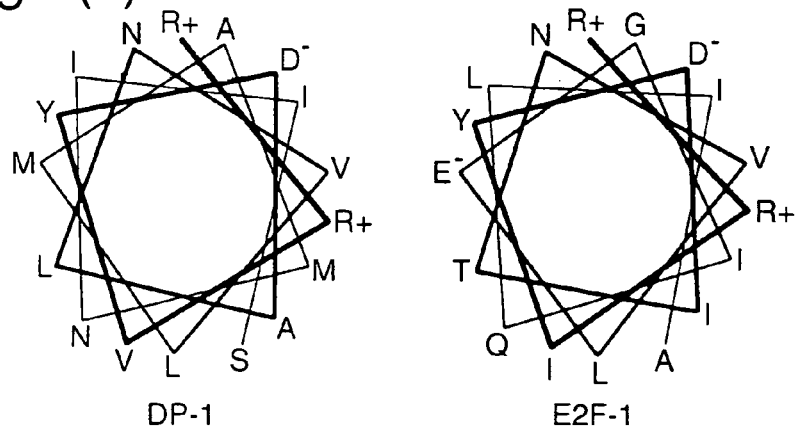
DP-1          E2F-1

Summary of Constructs

Reporters p3xWT p3xMT pCMVcat

Effectors pG4mpoly II pGB9

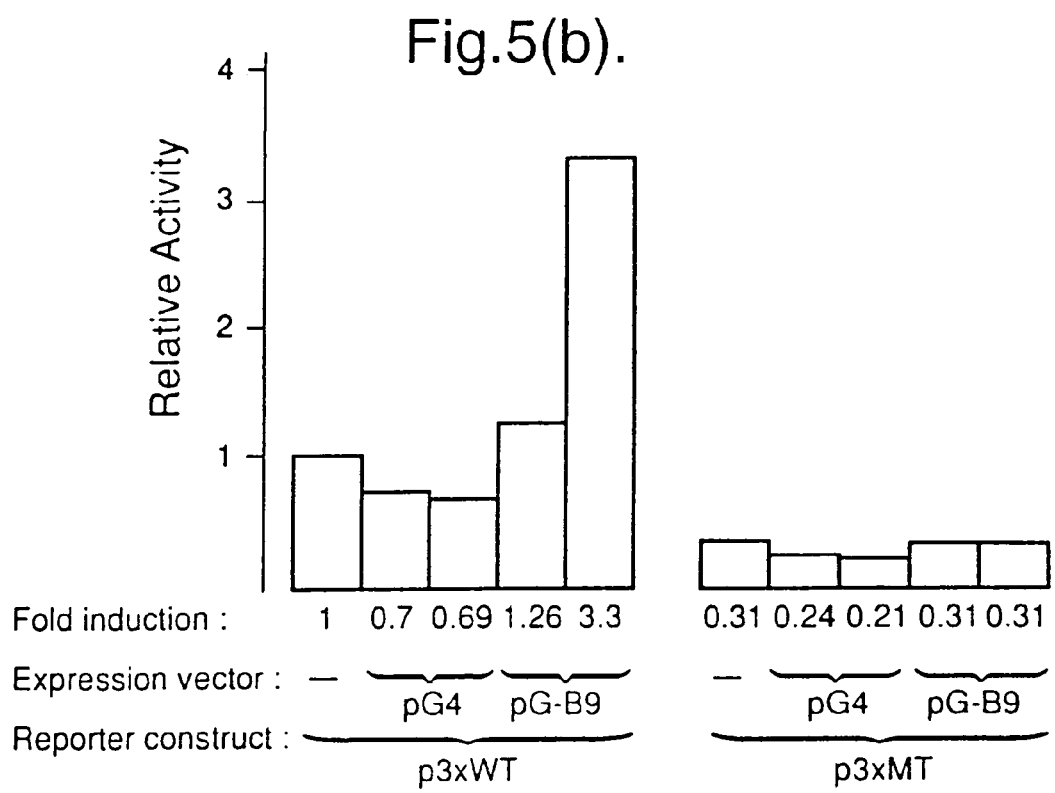
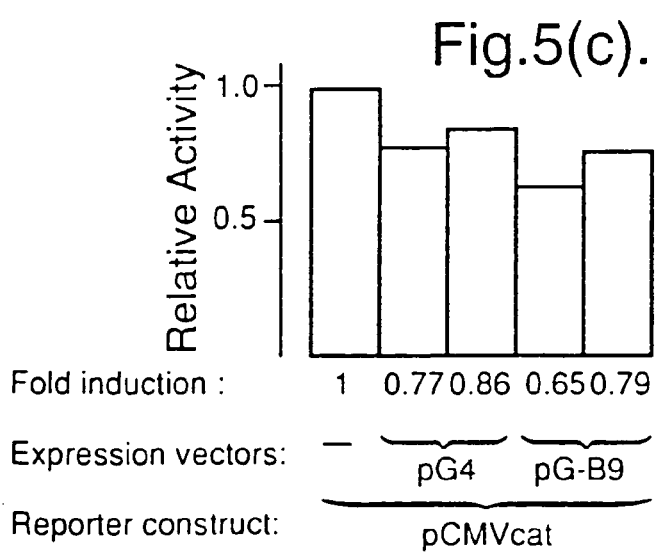

INTERACTION WITH E2F-1:

|  | DNA BINDING | DIMERIZATION |
|---|---|---|
| DP-1 84-249 | + + | + |
| DP-1 84-204 | + | + |
| DP-1 146-249 | − | + |
| DP-1 84-166 | − | − |

| Fold Induction: | 1 | 1.59 | 9.62 | 48.1 |
| Effector: | | DP-1 | E2F-1 | DP-1/E2F-1 |

Reporter  p4xWT CYC 1

TRANSCRIPTION FACTOR DP-1

The present application is a continuation of application Ser. No. 09/078,596, filed May 14, 1998, (now U.S. Pat. No. 6,150,116) which is a continuation of application Ser. No. 08/428,131, filed Jun. 23, 1995, (now U.S. Pat. No. 5,863,757) which is a 371 U.S. National Phase of PCT/GB93/02227, which designated the U.S., and was filed Oct. 29, 1993; which claims benefit of UK Application No. 9222715.6 filed Oct. 29, 1992, and UK Application No. 9316206.3, filed Aug. 5, 1993.

This invention relates to a novel transcription factor, to its production and uses.

The molecular events that occur during the cell cycle need to be integrated with the transcription apparatus so that gene expression can be snychronised with cell cycle progression. Recently, a transcription factor called DRTF1 or E2F has been identified and shown to bind to pRb, the protein product of the retinoblastoma susceptibility gene, an antioncogene or tumour suppressor gene (see for example Wagner and Green, Nature 352, 189–190, 1991). It is widely believed that the cellular transcription factor DRTF1/E2F functions as a key component in cell cycle control because it associates with important cell cycle regulating proteins, such as the retinoblastoma gene product (pRb), p107, cyclins and cyclin-dependent kinases, and furthermore its transcriptional activity is modulated by certain vial oncoproteins, such as adenovirus Ela, SV40 large T antigen, and the human papilloma virus E7 protein.

It is believed that the transcription factor DRTF1/E2F plays an important role in integrating cell cycle events with the transcription apparatus because, during cell cycle progression in mammalian cells, it undergoes a series of periodic interactions with molecules that are known to be important regulators of cellular proliferation. For example, the retinoblastoma tumour suppressor gene product (pRb), which negatively regulates progression from G1 into S phase and is frequently modified in tumour cells binds to DRTF1/E2F. Similarly, the pRb-related protein p107 occurs predominantly in an S phase complex with DRTF1/E2F. Both pRb and p107 repress the transcriptional activity of DRTF1/E2F, which is likely to be fundamentally important for regulating cellular proliferation because DRTF1/E2F binding sites (the E2F) site) occur in the control regions of a variety of genes that are involved with proliferation, such as c-myc and $p34^{cdc2}$. Furthermore, mutant Rb proteins, encoded by alleles isolated from tumour cells, fail to bind to DRTF1/E2F, and hence are unable to interfere with E2F site-dependent transcriptional activation. Another important feature of DRTF1/E2F is that certain viral oncoproteins, such as adenovirus Ela, SV40 large T antigen and human papilloma virus E7, modulate its activity by sequestering pRb and p107 from the inactive transcription factor. This effect requires regions in these viral proteins that are necessary for transformation of tissue culture cells and hence to overcome growth control. Thus, the ability of these oncoproteins to regulate DRTF1/E2F may be the means by which they over-ride the normal mechanisms of cellular growth control and, conversely, transcriptional repression by pRb may be the basis of pRb-mediated negative growth control.

A potential mechanism for integrating the transcription-regulating properties of pRb and p107 with other cell cycle events was suggested by the identification of cyclin A and the cdc2-related cyclin-dependent kinase $p33^{cdk2}$ in the DRTF1/E2F complex. Cyclin A is necessary for progression through S phase, a function that could perhaps be mediated through its ability to recruit the cyclin-dependent kinase $p33^{cdk2}$ to DRTF1/E2F. Taken together these data suggest that DRTF1/E2F is a transcription factor whose primary role may be to relay cell cycle events to the transcription apparatus via molecules such as pRb, p107, cyclins and cdks, thus ensuring that gene expression is synchronised and integrated with cell cycle progression.

More recently, a transcription factor with the properties of E2F has been cloned and sequenced (Helin et al, Cell 70 (1992), 337–350 and Kaelin et al, Cell 70 (1992), 351–364).

We have now surprisingly found that the protein termed E2F is a complex of factors, comprising the factor cloned by Helin et al and Kaelin et al, and a novel protein, whose cDNA sequence is presented below as SEQ ID NO: 2. The sequence of the cDNA encoding this protein is shown below as SEQ ID NO: 1. The new protein is referred to by us as DP-1. While not wishing to be bound by any one particular theory, it is believed that the factor cloned by Helin et al and Kaelin et al may dimerise with DP-1. Evidence presented in the accompanying examples shows that DP-1 and the protein of Helin et al (referred to as E2F-1) form a complex which is involved in the regulation of transcription.

It has also been found that E2F-1 is one of a family of related transcription factor components. Members of this family are believed to interact with DP-1 to form a series of above transcription factors.

BRIEF DESCRIPTION OF THE DRAWINGS

FIGS. 4a–4c show a comparison of DP-1 and E2F-1. The DP-1 sequences in FIGS. 4b and 4c are SEQ ID NOS: 11 and 13 respectively, and the E2F-1 sequences in FIGS. 4b and 4c are SEQ ID NOS: 12 and 14 respectively.

FIGS. 5a–5c summarize the constructs used and results obtained in experiments showing DP-1 activates E2F site dependent transcription in vivo.

Figure 1:
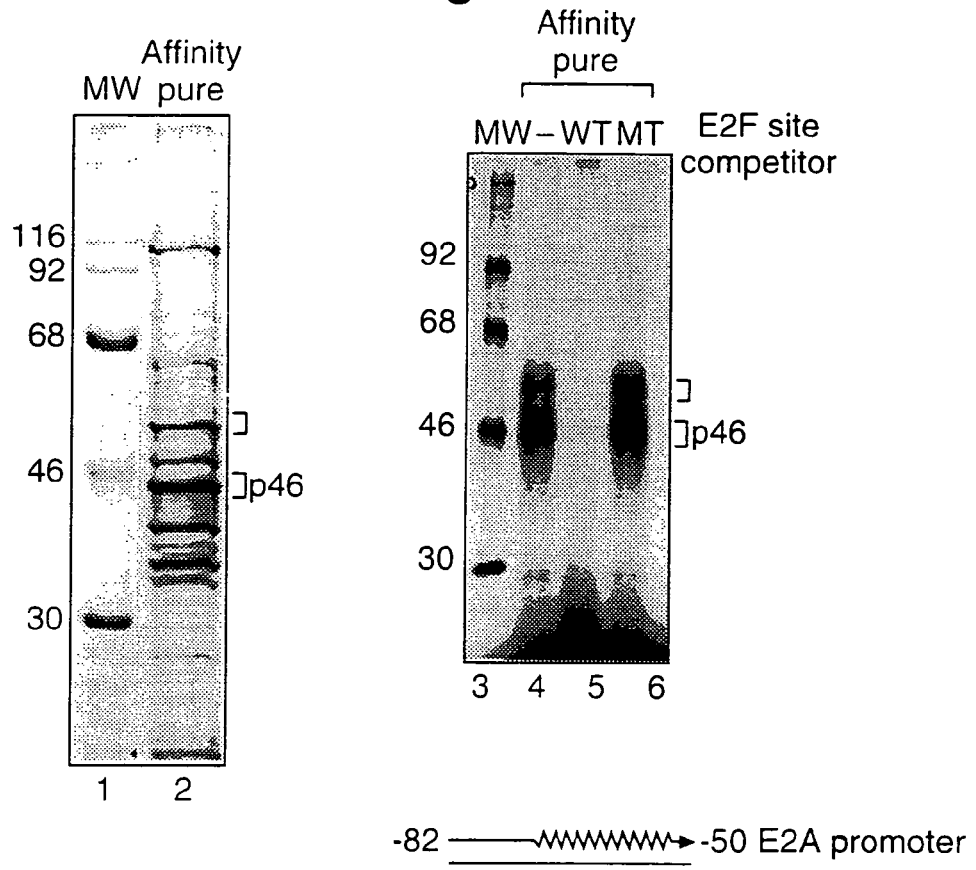
FIG. 1 shows the results of affinity purification of the DP-1 protein from F9 EC cells.

The present invention thus provides a polynucleotide in substantially isolated form which comprises a contiguous sequence of nucleotides which is capable of selectively hybridizing to SEQ ID NO: 1 or to the complement of SEQ ID NO: 1. A polynucleotide of the invention includes a DNA of SEQ ID NO: 1, and fragments thereof capable of selectively hybridizing to SEQ ID NO: 1. A further embodiment of the invention provides a DNA coding for the protein of SEQ ID NO: 2 or a fragment thereof.

The polynucleotide may also comprise RNA. It may also be a polynucleotide which includes within it synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purpose of the present invention, it is to be understood that the oligonucleotides described herein may be modified by any method available in the art. Such modifications may be carried out in order to enhance the in vivo activity or lifespan of oligonucleotides of the invention used in methods of therapy.

A polynucleotide capable of selectively hybridizing to the DNA of SEQ ID NO: 1 will be generally at least 70%, preferably at least 80 or 90% and more preferably at least 95% homologous to the DNA of SEQ ID NO: 1 over a region of at least 20, preferably at least 30, for instance at least 40, 60 or 100 or more contiguous nucleotides. Such a polynucleotide will be referred to below as a polynucleotide according to the invention.

A polynucleotide of the invention will be in substantially isolated form if it is in a form in which it is free of other polynucleotides with which it may be associated in the natural environment of the body. It will be understood that the polynucleotide may be mixed with carriers or diluents which will not interfere with the intended purpose of the polynucleotide and still be regarded as substantially isolated.

A polynucleotide according to the invention may be used to produce a primer, e.g. a PCR primer, a probe e.g. labelled with a revealing label by conventional means using radioactive or non-radioactive labels, or the polynucleotide may be cloned into a vector. Such primers, probes and other fragments of the DNA of SEQ ID NO: 1 will be at least 15, preferably at least 20, for example at least 25, 30 or 40 nucleotides in length, and are also encompassed by the term "a polynucleotide according to the invention" as used herein.

A polynucleotide such as a DNA polynucleotide according to the invention may be produced recombinantly, synthetically, or by any means available to those of skill in the art. It may be also cloned by reference to the techniques disclosed herein.

The invention further provides a double stranded polynucleotide comprising a polynucleotide according to the invention and its complement.

A further embodiment of the invention provides vectors for the replication and expression of a polynucleotide, in particular a DNA or RNA polynucleotide, according to the invention. The vectors may be, for example, plasmid, virus or phage vectors provided with an origin of replication, optionally a promoter for the expression of the said polynucleotide and optionally a regulator of the promoter. The vector may contain one or more selectable marker genes, for example an ampicillin resistance gene in the case of a bacterial plasmid or a neomycin resistance gene for a mammalian vector. The vector may be used in vitro, for example for the production of RNA or used to transfect or transform a host cell. The vector may also be adapted to be used in vivo, for example in a method of gene therapy.

A further embodiment of the invention provides host cells transformed or transfected with the vectors for the replication and expression of a polynucleotide according to the invention, including the DNA SEQ ID NO: 1 or the open reading frame thereof. The cells will be chosen to be compatible with the vector and may for example be bacterial, yeast, insect or mammalian.

A polynucleotide according to the invention may also be inserted into the vectors described above in an antisense orientation on order to provide for the production of antisense RNA. Antisense RNA or other antisense polynucleotides may also be produced by synthetic means. Such antisense polynucleotides may be used in a method of controlling the levels of the protein of SEQ ID NO: 2 in a cell. Such a method will include the step of introducing into the cell the antisense polynucleotide in an amount effective to inhibit or reduce the level of translation of the DP-1 mRNA into protein. The cell may be a cell which is proliferating in an uncontrolled manner such as a tumour cell.

The invention further provides a protein of SEQ ID NO: 2, homologues thereof, and fragments of the sequence and its homologues, which is capable of functioning as a mammalian transcription factor. In particular, the invention provides a polypeptide in substantially isolated form which comprises:
  (a) the protein of SEQ ID NO: 2; or
  (b) an allelic variant or species homologue thereof; or
  (c) a protein at least 70% homologous to (a); or
  (d) a fragment of any one of (a) to (c) capable of forming a complex with the E2F-1 protein or related family member; or
  (e) a fragment of any one of (a) to (c) of at least 15 amino acids.

All polypeptides within this definition are referred to below as a polypeptide according to the invention.

A polypeptide of the invention will be in substantially isolated form if it is in a form in which it is free of other polypeptides with which it may be associated in the natural environment of the body. It will be understood that the polypeptide may be mixed with carriers or diluents which will not interfere with the intended purpose of the polynucleotide and still be regarded as substantially isolated.

A polypeptide of the invention may also be in a substantially purified form, in which case it will generally comprise the polypeptide in a preparation in which more than 90%, eg. 95%, 98% or 99% of the polypeptide in the preparation is a polypeptide of the invention.

An allelic variant of a polypeptide of the invention will be a variant which will occur naturally in a murine animal and which will function to regulate gene expression in a substantially similar manner to the protein of SEQ ID NO: 2. Similarly, a species homologue of the protein will be the equivalent protein which occurs naturally in another species, including man, and which performs the equivalent function in that species to the DP-1 protein of SEQ ID NO: 2 in murine animals. Within any one species, a homologue may exist as several allelic variants, and these will all be considered homogogues of the SEQ ID NO: 2 protein. Allelic variants and species homologues can be obtained by following the procedures described herein for the production of the protein of SEQ ID NO: 2 and performing such procedures on a suitable cell source, eg from a rodent carrying an allelic variant or another species. Since the protein appears to be evolutionarily conserved it will also be possible to use a polynucleotide of the invention to probe libraries made from rodent or other cells in order to obtain clones encoding the allelic or species variants. The clones can be manipulated by conventional techniques to identify a polypeptide of the invention which can then be produced by recombinant or synthetic techniques known per se. Preferred species homologues include mammalian or amphibian species homologues.

A protein at least 70% homologous to the SEQ ID NO: 2 will be preferably at least 80 or 90% and more preferably at least 95% homologous to the protein of SEQ ID NO: 2 over a region of at least 20, preferably at least 30, for instance at least 40, 60 or 100 or more contiguous amino acids. Methods of measuring protein homology are well known in the art and it will be understood by those of skill in the art that in the present context, homology is calculated on the basis of amino acid identity (sometimes referred to as "hard homology").

Generally, fragments of SEQ ID NO: 2 or its allelic variants or species homologues thereof capable of forming a complex with the E2F-1 protein will be at least 10, preferably at least 15, for example at least 20, 25, 30, 40, 50 or 60 amino acids in length.

It will be possible to determine whether fragments form a complex with the E2F-1 protein by providing the E2F-1 protein and the fragment under conditions in which the E2F-1 protein and DP-1 normally form a trans-activating transcription factor, and determining whether or not a complex has formed. The determining may be made by, for example, measuring the ability of the complex to bind an E2F binding site in vitro, or alternatively, determining the molecular weight of the putative complex by methods such as SDS-PAGE.

Preferred fragments include those which are capable of forming a trans-activation complex with E2F-1 or its related family members. The examples herein describe a number of methods to analyse the function of the DP-1 protein and these may be adapted to assess whether or not a polypeptide is capable of forming a trans-activation complex with the E2F-1 protein. For example, the fragment can be added to E2F-1 in the presence of a reporter gene construct adapted to be activated by the DP-1/E2F-1 complex, as described in FIG. 10. Such an experiment will determine whether the polypeptide fragment has the necessary activity.

A polypeptide of the invention may be labelled with a revealing label. The revealing label may be any suitable label which allows the polypeptide to be detected. Suitable labels include radioisotopes, e.g. $^{125}$I, enzymes, antibodies and linkers such as biotin. Labelled polypeptides of the invention may be used in diagnostic procedures such as immunoassays in order to determine the amount of DP1 protein in a sample.

A polypeptide or labelled polypeptide according to the invention may also be fixed to a solid phase, for example the wall of an immunoassay dish.

The present invention also provides polynucleotides encoding polypeptides of the invention, for example double-stranded DNA polynucleotides. Such polynucleotides can be incorporated into a recombinant replicable vector. The vector may be used to replicate the DNA. Preferably, the DNA in the vector is operably linked to a control sequence which is capable of providing for the expression of the coding sequence by the host cell. The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences. Such vectors may be transformed into a suitable host cell as described above to provide for expression of a polypeptide of the invention.

Thus, in a further aspect the invention provides a process for preparing a polypeptide according to the invention which comprises cultivating a host cell transformed or transfected with an expression vector as described above under conditions to provide for expression by the vector of a coding sequence encoding the polypeptide, and recovering the expressed polypeptide.

The invention also provides monoclonal or polyclonal antibodies to a polypeptide according to the invention. The invention further provides a process for the production of monoclonal or polyclonal antibodies to the protein of SEQ ID NO: 2 or to a polypeptide of the invention. Monoclonal antibodies may be prepared by conventional hybridoma technology using the proteins or peptide fragments thereof, as an immunogen. Polyclonal or peptide fragments thereof, as an immunogen. Polyclonal antibodies may also be prepared by conventional means which comprise inoculating a host animal, for example a rat or a rabbit, with a peptide of the invention and recovering immune serum.

Fragments of monoclonal antibodies according to the invention which retain their antigen binding activity, such Fv, F(ab') and F(ab$_2$)' fragments form a further aspect of the invention. In addition, monoclonal antibodies according to the invention may be analyzed (eg. by DNA sequence analysis of the genes expressing such antibodies) and humanized antibody with complementarity determining regions of an antibody according to the invention may be made, for example in accordance with the methods disclosed in EP-A-0239400 (Winter).

The present invention also provides compositions comprising a polypeptide of the invention together with a carrier or diluent. Such compositions include pharmaceutical compositions in which case the carrier or diluent will be pharmaceutically acceptable.

The present invention further provides compositions comprising an antibody or fragment thereof of the invention together with a carrier or diluent. Such compositions include pharmaceutical compositions in which case the carrier or diluent will be pharmaceutically acceptable.

Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and the, if necessary, shaping the product.

For example, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the polypeptide to blood components or one or more organs.

Peptides according to the invention, antibodies or fragments thereof to peptides according to the invention and the above-mentioned compositions may be used for the treatment, regulation or diagnosis of conditions, including proliferative diseases, in a mammal including man. Such conditions include those associated with abnormal (eg at an unusually high or low level) and/or aberrant (eg due to a mutation in the gene sequence) expression of one or more transcription factors such as the E2F factor cloned by Helin et al or the protein of SEQ ID NO: 2 or the E2F-1 protein or related family members. The conditions also include those which are brought about by abnormal expression of a gene whose gene product is regulated by the protein of SEQ ID NO: 2. Treatment or regulation of conditions with the above-mentioned peptides, antibodies, fragments thereof and compositions will usually involve administering to a recipient in need of such treatment an effective amount of a polypeptide, antibody, fragment thereof or composition.

One group of preferred polypeptides according to the invention are those which are based upon the region of amino acids 160–220 of SEQ ID NO: 2. This region of the protein has a homology of about 40% to a similar region of the E2F-1 protein described by Helin et al (ibid) and both regions are putative alpha-helical regions. While not wishing to be bound by any one particular theory, we believe that the heterodimerisation of E2F and the protein according to the invention is mediated through these homologous regions. Accordingly, a preferred embodiment of the invention is to polypeptides of the invention based upon this region, and pharmaceutical compositions containing such polypeptides, for use in a method of inhibiting the activation of transcription factors via the disruption of the formation of the E2F-1-SEQ ID NO: 2 protein complex.

The invention also provides antibodies, and fragments thereof, targeted to this region of SEQ ID NO: 2 in order to achieve the above described effect.

The present invention further provides an immunoassay for detecting the presence or absence of a polypeptide of the invention in a sample which comprises:
  (a) providing an antibody according to the invention;
  (b) incubating the sample with said antibody under conditions that allow for the formation of an antibody-antigen complex; and
  (c) detecting said antibody-antigen complex.

In another aspect, the invention provides a novel assay for identifying putative chemotherapeutic agents for the treatment of proliferative or viral disease which comprises bringing into contact E2F-1 protein or a derivative thereof a polypeptide of the invention and a putative chemotherapeutic agent, and measuring the degree of inhibition of formation of the E2F-1-SEQ ID NO: 2 protein complex caused by the agent. It may not be necessary to use complete E2F-1 and/or SEQ ID NO: 2 protein in the assay, as long as sufficient of each protein is provided such that under the conditions of the assay in the absence of agent, they form a heterodimer. Thus, the invention provides a screening method for identifying putative chemotherapeutic agents for the treatment of proliferative disease which comprises
  (A) bringing into contact:
    (i) a polypeptide according to the invention,
    (ii) (a) the E2F-1 protein, or (b) an allelic variant or species homologue thereof, or (c) an E2F-1 family member having at least 70% homology over the DNA binding region, or (d) a fragment of (a), (b) or (c) capable of forming a functional trans-activation complex with the protein of SEQ ID NO: 2; or (e) a fusion protein comprising (a), (b), (c), or (d); and
    (iii) a putative chemotherapeutic agent; under conditions in which the components (i) and (ii) in the absence of (iii) form a complex, and
  (B) measuring the extent to which component (iii) is able to disrupt said complex. In the assay, any one or more of the three components may be labelled, eg with a radioactive or colorimetric label, to allow measurement of the result of the assay. Putative chemotherapeutic agents include peptides of the invention.

Variants, homologues and fragments of E2F-1 protein are defined in a corresponding manner to the variants, homologues and fragments of the DP-1 protein.

The complex of (i) and (ii) may be measured, for example, by its ability to bind an E2F DNA binding site in vitro. Alternatively, the assay may be an in vivo assay in which the ability of the complex to activate a promoter comprising an E2F binding site linked to a reporter gene is measured. The in vivo assay may be performed for example by reference to the examples which show such an assay in yeast, insect, amphibian or mammalian cells.

Candidate therapeutic agents which may be measured by the assay include fragments of 10 or more amino acids of
  (a) the protein of SEQ ID NO: 2
  (b) an allelic variant or species homologue thereof; or
  (c) a protein at least 70% homologous to (a).

Vectors carrying a polynucleotide according to the invention or a nucleic acid encoding a polypeptide according to the invention may be used in a method of gene therapy. Such gene therapy may be used to treat uncontrolled proliferation of cells, for example a tumour cell. Methods of gene therapy include delivering to a cell in a patient in need of treatment an effective amount of a vector capable of expressing in the cell either an antisense polynucleotide of the invention in order to inhibit or reduce the translation of DP-1 mRNA into DP-1 protein or a polypeptide which interferes with the binding if DP-1 to E2F-1 or a related family member.

The vector is suitably a viral vector. The viral vector may be any suitable vector available in the art for targeting tumour cells. For example, Huber et al (Proc. Natl. Acac. Sci. USA (1991) 88, 8039) report the use of amphotropic retroviruses for the transformation of hepatoma, breast, colon or skin cells. Culver et al (Science (1992) 256; 1550–1552) also describe the use of retroviral vectors in virus-directed enzyme prodrug therapy, as do Ram et al (Cancer Research (1993) 53; 83–88). Englehardt et al (Nature Genetics (1993) 4; 27–34 describe the use of adenovirus based vectors in the delivery of the cystic fibrosis transmembrane conductance product (CFTR) into cells.

It has also been found that the protein of SEQ ID NO: 2 is distributed in the cell in both the cytoplasm and the nuclei. In order for a protein to be transported from the cytoplasm to the nuclei, it is usual for processing of the protein to occur, for example by phosphorylation or proteolytic clipping. Compounds which inhibit phosphorylation are known in the art. Compounds which inhibit proteolytic clipping may include peptides of the invention which act as antagonists to inhibit enzymes responsible for clipping. Thus, in a further aspect, the present invention provides a compound which inhibits phosphorylation or proteolytic clipping for use in a method of inhibiting transport of the protein of SEQ ID NO: 2 from the cytoplasm to the nucleus of a cell.

The following examples describe the isolation and characterization of the novel protein and DNA of the invention from a murine source. However, other sources, e.g. human or other mammalian are within the scope of the present invention and the human or other mammalian homologues of the protein may be isolated in an analogous manner.

EXAMPLES

Section A

Affinity Purification of DRTF1/E2F from F9-EC Cells

Polypeptides in affinity purified DRTF1/E2F (approximately 5 µg from about $5 \times 10^{10}$ F9 EC cells) were separated by SDS gel electrophoresis and stained with coomassie blue as shown in FIG. 1 (track 2); track 1 shows the molecular weight standards. DNA binding polypeptides in affinity purified DRTF1/E2F were assayed by cross-linking to the adenovirus E2A promoter distal E2A site (binding site details indicated in the figure) either in the absence (track 4) or presence of competing wild-type (track 5) or mutant (track 6) E2F binding sites; molecular weight standards are shown in track 3. The p46 polypeptide is indicated; the upper bracket shows another group of polypeptides which also specifically bind to the E2F site of approximate molecular weight 55,000.

Methods: DRTF1/E2F was affinity purified from whole cell extracts prepared from F9 EC cells as described by Shivji and La Thangue (1991) Mol. Cell. Biol. 11, 1686–1695 using affinity matrices containing the wildtype E2F site taken from the adenovirus E2A promoter (−70 to −50) with inclusion of an additional step that involved application of the binding activity to a matrix containing a mutant E2F binding site (mutated in nucleotides −62 to −60). On average about 5.0 µg of protein were purified from a whole cell extract prepared from about $10^{10}$ F9 EC cells. UV-crosslinking of DRTF1/E2F to the E2F site was performed using about 50 ng of affinity purified protein. Competition was performed with about 100-fold molar excess of either the wildtype (−71 to −50) or mutant (mutated in nucleotides −62 to −60) oligonucleotides.

Nucleotide Sequence of a cDNA Encoding Murine DP-1

Affinity purified DRTF1 was precipitated with TCA, electrophoresed through an SDS polyacrylamide gel and p46 was electroeluted; the purity of p46 was confirmed by electrophoresis and silver staining a small sample of the eluted material. p46 was digested with a lysylendopeptidase, and peptides purified by high performance liquid chromatography using Aquapore AX-300 and RP-300 in series in 0.1% TFA with a 1%/min acetonitrile gradient. Peak fractions were sequenced by automated Edman degradation in a 477A/120A gas-liquid pulse sequencer (Applied Biosystems Inc.).

A set of degenerate oligonucleotide primers were synthesised on the basis of the amino acid sequence in peptides 6 (75 to 91) and 5 (235 to 243) as follows: the C-terminal regions of peptide 6 (PNTHFV) (SEQ ID NO: 3) CGCG-GATCCCC(ACGT) AA (CT) AC(ACGT) CA (CT) TT (CT) GT 3' (SEQ ID NO: 4) and peptide 5 (AQESQN) (SEQ ID NO: 5), antisense strand 5'CGCGGATCCA (AG) (AG) TT (CT) TG (ACGT) (CG) (AT)—(CT) TC (CT) TG (ACGT) GC 3' (SEQ ID NO: 6); both oligonucleotides included a linker sequence at the 5' end. Peptide 5 antisense oligonucleotide was used to synthesise cDNA from F9 EC cell RNA which was then used in a PCR with both peptide 6 and 5 primers. Products were subcloned, sequenced and cDNAs derived from DP-1 RNA identified by the presence of peptides 21 and 3, two further peptides obtained by microsequencing peptides derived from p46, which are located between peptides 6 and 5. This cDNA fragment was used to screen several murine cDNA libraries. DP-1 cDNA clones were frequently rearranged and the final nucleotide sequence shown in the figure was obtained from cDNAs isolated from an F9 EC cell library.

DP-1 is a DNA Binding Polypeptide in DRTF1/E2F and associates with pRb in vivo

Peptide 15 (representing DE-1 amino acid residue 235 to 249) and peptide A (representing DF-1 amino acid residue 3 to 15) were coupled to KLH and used to immunise rabbits. The generation of antibodies and immunoblotting were performed by standard procedures. In gel retardation assays about 5.0 ng of affinity purified DRFT1/E2 F or about 5.0 µg of F9 EC crude cell extract were assayed with either the wildtype E2A promoter (−96 to 68) or an oligonucleotide containing E2A promoter sequences −71 to −50 in the presence of about 100-fold molar excess of −62/−60 (E2A sequences −71 to −50 mutated in positions −62, −61 and −60 (ref. 23). Anti-peptide A or preimmune sera were added during the preincubation period. Immunoprecipitation of pRb from JM whole cell extracts was performed by standard procedures. The presence of pRb in IF8 immunoprecipitates was confirmed by immunoblotting. The results are shown in FIG. 2 as follows:

a) DP-1 is present in affinity pure DRTF1/E2F: immunoblot with affinity purified DRTF1/E2F and anti-peptide 15 (amino acid residues 235 to 249). Reactivity with p46 and p55 was only present in the immune (I, track 2) but not preimmune (PI, track 3) serum. This was specific because it was competitively inhibited by peptide 15 but not an unrelated peptide, peptide 1 (compare tracks 6 and 5). p46 is likely to be a derivative of p55 (indicated in track 3) because anti-peptide A (see below, derived from the N-terminal region of DP-1) only detected p55 (data not shown). Molecular weight standards are shown in track 1, and the * indicates a non-specific reaction.

b) DP-1 is in the affinity pure DRTF1/E2F DNA binding complex: gel retardation was performed with affinity purified DRTF1/E2F and the adenovirus E2A promoter (−96 to +68) in the presence of immune (tracks 3 to 6) or preimmune (track 2) anti-peptide A together with either unrelated peptide 1 (tracks 4 and 6) or peptide 15 (track 5). The specificity of the binding reaction was confirmed by including 100-fold molar excess of the wild-type E2F binding site (E2A promoter −71 to −50) in the reaction (track 6); all other reactions contained 100-fold excess of the mutant site.

c) DP-1 is in the DRTF1/E2F DNA binding complex in F9 EC cell extracts: gel retardation was performed in F9 EC whole cell extracts (in which DRTF1/E2F resolves as complexes a, b and c) with an E2F binding site (E2A promoter sequences −71 to −50) in the presence of either preimmune (track 2) or immune (track 3) anti-peptide A serum. The super shift was prevented by including peptide A in the binding reaction (compare duplicate tracks 7 and 8 to 9 and 10).

(d) DP-1 associates with pRb in vivo: an immunoprecipitation was performed from JM cell extracts with either the anti-pRb monoclonal antobody IF8 or a control monoclonal antibody A7. The immunoprecipitates were treated with 1.0% deoxycholate (DOC) and the detergent-released material assayed for DRTF1/E2F activity in a gel retardation as described above. DRTF1/E2F binding activity was only detected in the anti-pRb immunoprecipitates (compare tracks 2 to 3); the JM cell extract depleted with anti-pRb had reduced levels of the pRb complex (compare tracks 4 to 5, complex indicated by a). The detergent-released DRTF1/E2F was further assayed for reactivity with anti-peptide A; the immune but not the preimmune serum produced a super shift (compare tracks 6 to 7; indicated by *).

DP-1 is a Sequence Specified DNA Binding Protein

Regions of the DP-1 cDNA were amplified in a PCR and subcloned into pGEX-2T (14). GST-DP-1$^{84-204}$ and GST-cdk2 were affinity purified on glutathione-Sepharose as previously described by Bandara et al (1991) Nature, 352, 249–251 Gel retardation was performed as described above with either the E2A promoter or an oligonucleotide containing E2A sequences from −82 to −50; the mutant binding site had nucleotides −62, −61 and −60 altered. UV-crosslinking was performed with about 5.0 µg of GST fusion protein.

a) The GST fusion protein described in the cartoon, GST-DP-1$^{84-204}$, which contains DP-1 protein sequence from amino acid residue 84 to 204, was expressed and affinity purified to homogeneity. Track 1 shows the affinity purified DP-1$^{84-204}$ and track 2, the standard molecular weight markers.

b) DP-1 binds to the E2F binding site: affinity purified GST-DP-1$^{84-204}$ (about 1.0 µg) was incubated with either the E2A promoter (track 2), or oligonucleotides (WT and MT binding site details at the bottom of the figure) containing E2A promoter sequence −82 to −50 (track 5) or the same containing a mutant E2F site (track 8). A control GST fusion protein, GST-cdk2 (about 1.0 µg), had no binding activity (tracks 3, 6 and 9); tracks 1, 4 and 7 contain no protein.

c) Crosslinking DP-1 to DNA: affinity purified GST-DP-1$^{84-204}$ (track 4) or GST-cdk2 (track 3) was incubated with E2A promoter sequences −82 to −50 (indicated at bottom of tracks). After crosslinking, polypeptides were resolved by SDS gel electrophoresis; crosslinked GST-DP-1$^{84-204}$ is indicated by the bracket. No fusion protein was added in track 2 and the molecular weight standards are indicated in track 1.

d) Binding properties of DP-1 in affinity purified DRTF1/E2F: binding of purified GST-DP-1$^{84-204}$ or the control fusion protein GST-cdk2 to the E2A promoter was assayed either along (tracks 5 and 6; about 1.0 µg) or in the presence of affinity pure DRTF1/E2F (tracks 3 and 4; about 5.0 ng); the binding activity of the same amount of affinity pure DRTF1/E2F is assayed along in track 2; the E2A promoter is shown in track 1. Note that the binding characteristics of GST-DP-1$^{84-204}$ and DRTF1/E2F are different when assayed together (compare tracks 2, 3 and 5).

Comparison of DP-1 and E2F-1

This is shown in FIG. 4 as follows:

a) Line diagram of DP-1 and E2F-1 showing the location of the DNA binding domains (amino acid residues 84 to 204 in DP-1, and 89 to 191 in E2F-1; see ref. 24) and a region of significant similarity (amino acid residues 163 to 236 in DAP-1, and 162 to 226 in E2F-1). Note that the region of similarity includes sequences outside the DNA binding domain.

b) Alignment of amino acid sequence: comparisons of DP-1 (top) and E2F-1 (bottom) sequence in regions of similarity. Bars indicate identical (bold) or similar (light) amino acid residues.

c) The DP-1 and E2F-1 regions of similarity form an amphipathic α helix. Presentation of DP-1 (right; amino acids 167 to 183) and E2F-1 (left; amino acids 166 to 182) regions of similarity as a helical wheel.

DP-1 Activates E2F Site-dependent Transcription in vivo

Either 2.0 or 6.0 µg of pG4, or 2.8 or 8.8 µg of pG-B9 (DP-1 expression vector) were co-transfected with either p3xWT (5.0 µg), p3xMT (5.0 µg) or pCMVcat (0.5 µg) into SAOS-2 cells as indicated in FIG. 5 (constructs indicated in a). p3xWT and p3xMT reporter constructs contain either three wildtype or three mutant E2F binding sites, taken from the adenovirus E2A promoter (−71 to −50, mutated at nucleotides −62, −61 and −60), positioned upstream of the minimal herpes simplex virus thymidine kinase promoter, and have been described previously. pCMVcat contains the enhancer and promoter region (−301 to +72) taken from the immediate early gene of human cytomegalovirus. pG-B9 contains DP-1 protein sequence from amino acid residue 63 to 429, and was prepared by replacing the Gal4 DNA binding domain in pG4mpolyII with the DP-1 cDNA B9. Transfection into SAOS-2 cells was performed, and CAT activity was determined and TLC plates quantitated by phosphorimager.

Isolation of a cDNA Encoding DP-1

DRTF1 was purified from F9 EC whole cell extracts using a high stringency procedure that involved sequential applications to a DNA binding site affinity matrix containing either a wild-type or mutant binding site, and assaying the DNA binding activity by gel retardation (26). The DNA binding site was taken from the adenovirus E2A promoter (−71 to −51), a region that contains a high affinity E2F binding site (23). This procedure routinely purified a group of polypeptides (FIG. 1, track 2) that were capable of efficiently activating transcription in vitro in a binding site-dependent fashion. Several polypeptides in the affinity purified material specifically bound to the wildtype but not to the mutant E2F site (FIG. 1, compare tracks 5 to 6). The most abundant polypeptide that specifically bound had an apparent molecular weight of about 46 kD (FIG. 1, track 2, indicated as p46). Subsequently, p46 was excised, digested with a lysylendopeptidase, and the resulting peptides purified and sequenced; the amino acid sequence for ten peptides was obtained. We predicted the DNA sequences that encode two of the peptides and then used these as oligonucleotide primers to amplify a cDNA fragment derived from F9 EC RNA. Several murine cDNA libraries were screened with the cloned cDNA fragment, and a clone representing the complete coding sequence of p46 (from now on referred to as DP-1) finally isolated from an F9 EC cDNA library.

Molecular Properties of DP-1

The complete DP-1 coding sequence was determined from a 2.4 kb cDNA fragment. This cDNA contained an open reading frame encoding 429 in frame amino acid residues that included eight of the peptides obtained from sequencing p46. The cDNA sequence probably includes the initiating methionine because an inframe termination codon exists immediately upstream of it and, moreover, the nucleotides flanking and including this methionine would be an efficient translation initiation signal. The longest cDNA clone isolated so far extends 55 nucleotides 5' from this predicted initiating methionine. However, it does not extend to the transcription initiation site because primer extension analysis with F9 EC cell RNA has indicated that the initiation site is 250 nucleotides upstream. The cDNA also contains about 1.1 kb of 3' untranslated sequence, part of which is presented.

By northern analysis of poly adenylated F9 EC RNA the size of the DP-1 transcript was estimated to be about 2.6 kb. It was observed that DP-1 RNA is constitutively expressed in many different cell types and when assessed by in situ hybridization in a wide range of tissues during murine embryogenesis. During F9 EC cell differentiation, it was found that DP-1 RNA is marginally down-regulated as F9 EC stem cells differentiate. Southern analysis indicated that DP-1 is encoded by a single gene.

Homology searches of the currently available protein data bases (Leeds and Swiss) failed to detect any significant similarity between DP-1 and any other protein. However, we noticed that a small region within the DNA binding domain of DP-1 has significant similarity to an analogous region in the DNA binding domain of E2F-1 (see later), a recently characterised protein that also binds to the E2F site.

Characterisation of DP-1

To confirm that DP-1 is a component of DRTF1/E2F and to determine whether it is present in the DRTF1/E2F DNA binding complex, a number of anti-peptide antisera were raised against different regions of the DP-1 protein (FIG. 2). Immunoblotting affinity purified DRTF1/E2 F with anti-peptide 15 revealed two polypeptides with apparent molecular weight 46 kD and 55 kD (FIG. 2a, track 2). Both polypeptides were specifically recognised by the antiserum because the reaction was competitively inhibited by peptide 15 but not by an unrelated peptide, peptide 1 (FIG. 2a, compare tracks 5 and 6).

Figure 2A:
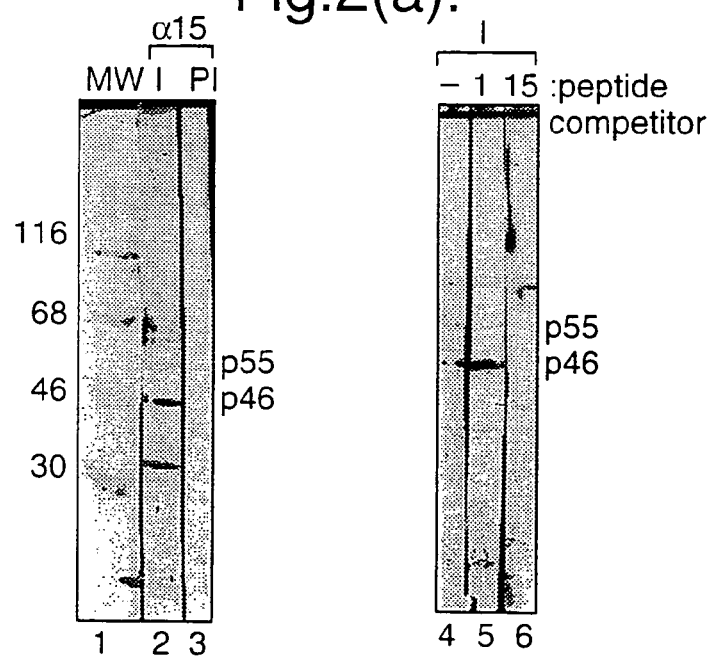
FIGS. 2a–2d show DP-1 is a DNA binding polypeptide in the E2F complex.
Figure 2B:
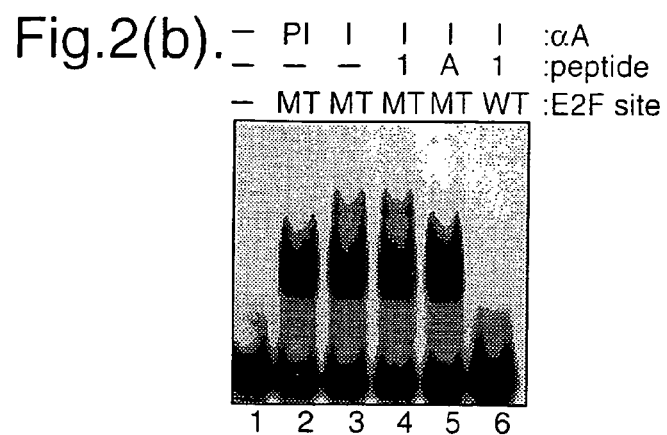

It was confirmed that DP-1 was part of the DRTF1/E2F DNA binding complex by determining the effect that another anti-peptide (anti-peptide A) had in gel retardation assays; anti-peptide 15 could not be used for these assays because it only reacts with the denatured protein. When anti-peptide A was incubated with affinity purified DRTF1/E2F a super-shift was apparent with the immune but not preimmune serum (FIG. 2b, compare tracks 2 and 3). This super-shift was specific because it was competitively inhibited by including peptide A but not the unrelated peptide 1 (FIG. 2b, compare tracks 4 and 5). Since all the binding activity resolved in these gel retardation conditions was specific for the E2F binding site (FIG. 2b, compare track 4 to 6), these results indicate that DP-1 is part of the DRTF1/E2F DNA binding activity.

Figure 2C:
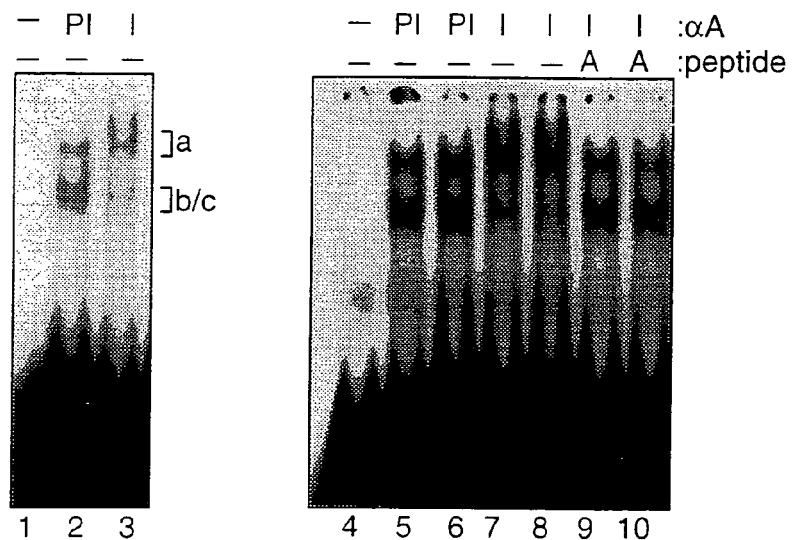

The anti-peptide antibodies also caused a super-shift in whole cell extracts. In F9 EC cell extracts DRTF1 resolves as a series of DNA-protein complexes, referred to as DRTF1a, b, and c. The addition of anti-peptide A, but not the preimmune serum, caused a supershift and a concommitant reduction in DRTF1a, b and c (FIG. 2c, compare tracks 2 and 3) which could be competed by peptide A (FIG. 2c, compare tracks 7 and 8 to 9 and 10). Similar effects were apparent in a wide variety of whole cell extracts derived from other types of cells, including HeLa. This suggests that DP-1 is a component of the DNA binding activity, DRTF1/E2F, that was initially defined in F9 EC cell extracts and which was also characterised in HeLa cell extracts.

DP-1 Associates with the Retinoblastoma Gene Produce in vivo

Figure 2D:
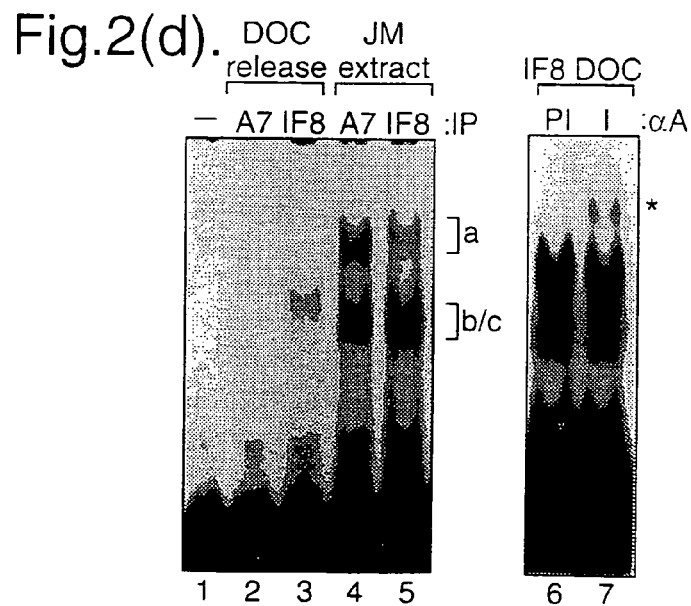

DRTF1/E2F binds to pRb both in vitro and in vivo. To determine if DP-1 associates with pRb. in vivo an immunoprecipitation experiment was performed with the anti-pRb monoclonal antibody IF8 from whole cell extracts prepared from the human leukaemic cell line JM, which contains high levels of the DRTF1/E2F-pRb complex. After immunoprecipitation, DRTF1/E2F DNA binding activity was released from pRb by treating the immune complex with mild detergent. In these conditions, DRTF1/E2F DNA binding activity was released only from the pRb immunoprecipitate, and not the control antibody immunoprecipitate (FIG. 2d, compare tracks 2 and 3). The presence of DP-1 in pRb-associated DRTF1/E2F was confirmed by treating the detergent release with anti-peptide A which caused DRTF1/E2F to supershift (FIG. 2d, compare tracks 6 and 8, indicated by *). This demonstrates that DP-1 associates with pRb in vivo.

DP-1 Specifically Binds to an E2F Site and has a Novel DNA Binding Domain

Figure 3A:
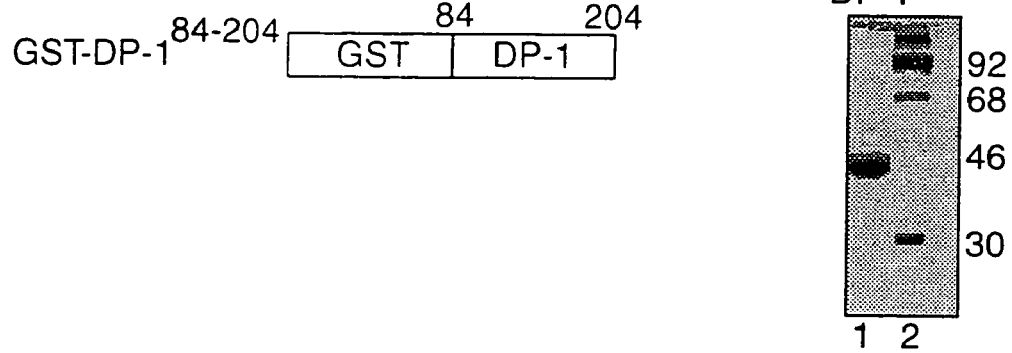
FIGS. 3a–3d show sequence specific DNA binding of DP-1.
Figure 3B:
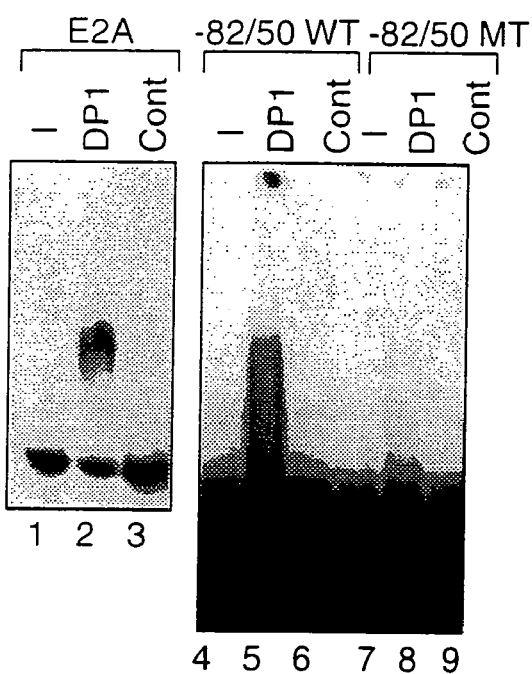
Figure 3C:
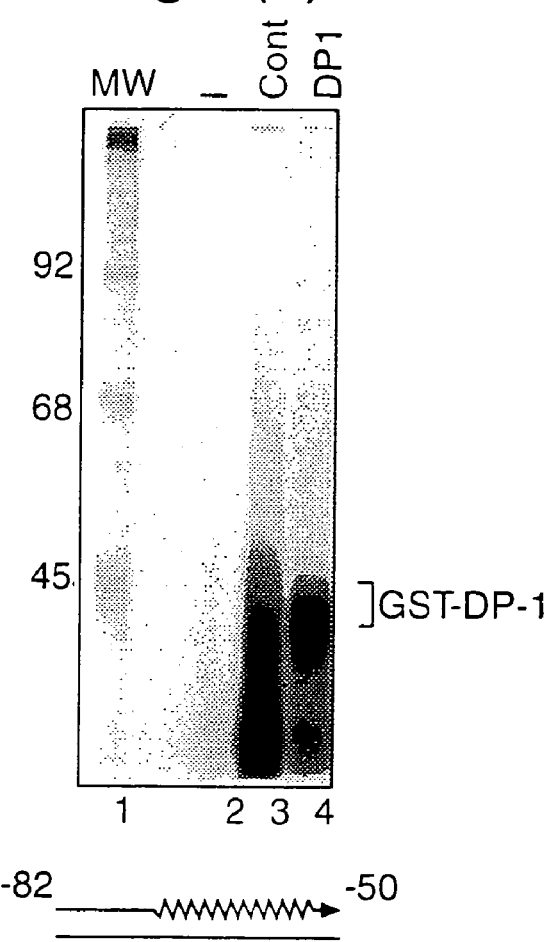

In order to determine whether DP-1 could bind to the E2F site in a sequence-specific fashion, regions of DP-1 coding sequence were expressed as glutathione-S-transferase (GST) fusion proteins, affinity purified, and tested for DNA binding activity. The smallest region so far defined that retains DNA binding activity contains DP-1 protein sequence from amino acid residue 84 to 204 (FIG. 3a; GST-DP-1$^{84-204}$); this bound to the adenovirus E2A promoter whereas an unrelated GST fusion (GST-cdk2) failed to do so (FIG. 3b; compare tracks 2 and 3). Furthermore, the DNA binding activity was specific for the E2F site because GST-DP-1$^{84-204}$ bound more efficiently to the wildtype than to the mutant E2F site (FIG. 3b, compare tracks 5 to 8). Thus DP-1 has similar DNA binding specificity as DRTF1/E2F in whole cell extracts and p46 in affinity pure DRTF1/E2F; the control GST fusion protein lacked any DNA binding activity (FIG. 3b, compare tracks 6 to 9). An anti-GST serum altered the mobility of the DP-1/DNA complex, confirming the presence of GST-DP-1$^{84-204}$ in the DNA binding complex. Furthermore, GST-DP-1$^{84-204}$ shared another property with p46 in that it could be specifically cross-linked to the E2F site (FIG. 3c, compare tracks 3 to 4). DP-1 therefore binds to the E2F site in a sequence-specific fashion and is thus likely to be a polypeptide in DRTF1/E2F that contributes to the DNA binding specificity.

Attempts to define the DNA binding domain more precisely have proved unsuccessful. Thus, this region of DAP-1 is likely to be close to the minimal amount of protein that allows sequence specific recognition and therefore, in all probability, defines the DNA binding domain. Overall, it is unrelated to any other type of DNA binding structure so far identified, and thus represents a new class of DNA binding domain. A small region (DP-1 amino acid residue 160 to 200) that has significant similarity to a region that lies within the DNA binding domain of E2F-1 (FIG. 4a), where 42% of the amino acid residues are identical and 70% similar (FIG. 5b) was noted. Secondary structure predictions suggests that these regions include two α helices, one of which is amphipathic (represented as a helical wheel in FIG. 4c). Since DP-1 and E2F-1 bind to the same DNA sequence, this region of similarity appears to be involved in recognising the DNA sequence that constitutes an E2F binding site.

The potential similarity of two other DNA binding proteins that regulate transcription during the yeast cell cycle supports this finding. Thus, the budding and fission yeast cell cycle-regulating proteins, encoded by SWI4 and cdc10, bind to a DNA sequence that resembles the E2F site, and contain a region within their DNA binding domains that has features in common with the DP-1/E2F-1 α helical region discussed above (FIG. 4c). Based on the above, this SWI4/cdc10 protein domain may also be involved in DNA sequence recognition.

Another region of similarity between DP-1 and E2F-1 is apparent outside the DNA binding domain (DP-1 amino acid residue 210 to 240, with 41% identical amino acid residues; FIG. 4b) which, like the earlier region, may form an amphipathic α helix. This region may contribute to DNA binding activity.

Figure 3D:
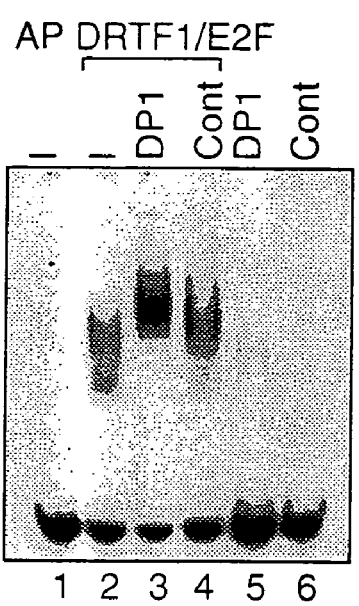

DP-1$^{84-204}$ may also contain a protein dimerisation interface because the addition of GST-DP-1$^{84-204}$ to affinity purified DRTF1/E2F resulted in a slower migrating protein-DNA complex relative to either GST-DP-1$^{84-204}$ or affinity purified DRTF1 alone, whereas a control GST-fusion protein had little effect (FIG. 3d). The slower migrating complex is likely to result from the interaction of GST-DP-1$^{84-204}$ with another protein in affinity purified DRTF1/E2F through a dimerisation domain contained within DP-1$^{84-204}$. The similarity between DP-1 and E2F-1 protein sequences within this region suggests that E2F-1 is a strong candidate for such a dimerisation partner.

DP-1 Activates Transcription in vivo

Figure 5A:
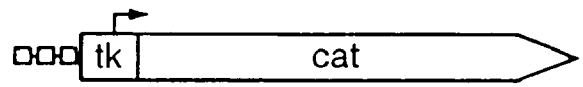
Figure 5A:
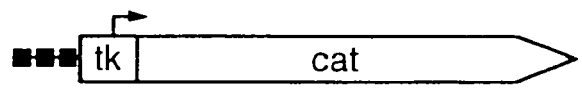
Figure 5A:
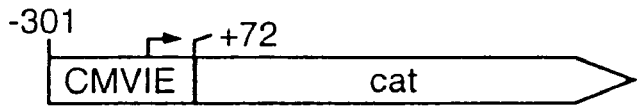
Figure 5A:
Figure 5A:
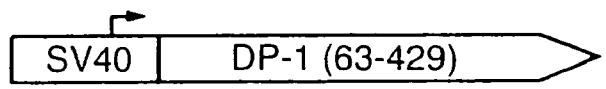

The E2A promoter distal E2F site (−71 to −50) functions as an activating sequence in a variety of cell types, such as SAOS-2 and F9 EC cells, when positioned upstream of the minimal herpes simplex virus thymidine kinase promoter. To determine if DP-1 can trans activate transcription through the E2F site, the effect of expressing the DP-1 coding sequence (amino acid residue 63 to 429) on the transcriptional activity of p3xWT and p3xMT, reporter constructs that are driven by either three wildtype or three mutant E2F binding sites respectively (FIG. 5a) was assessed. In SACS-2 cells, co-transfection of pG-B9 with p3xWT stimulated the transcriptional activity of p3xWT, whereas there was no effect of the plasmid pG4 (FIG. 5b). Transcriptional activation by pG-B9 was dependent on wildtype E2F sites because the activity of either p3xMT or pCMVcat was not significantly affected in the same transfection conditions (FIGS. 5b and c). This shows that DP-1 specifically activates transcription through a wildtype E2F site.

Thus, DP-1 is a sequence specific DNA binding protein that is present in DRTF1/E2F complexes assayed in extracts prepared from a variety of cell types and tissues.

Both pRb and p107 bind to DRTF1/E2F in a cell cycle-dependent fashion, an interaction that causes a reduction in the transcriptional activity of DRTF1/E2F. These complexes, together with the free transcriptionally active form of DRTF1/E2F, can be resolved in extracts from asynchronous cultures of tissue culture cells.

A striking feature of the DP-1 protein is its similar organisation to E2F-1, a recently described protein which also has properties similar to DRTF1/E2F. Thus, their DNA binding domains and regions of similarity are located in very similar positions (FIG. 4a) although the rest of the proteins are very different. It appears that DP-1 and E2F-1 exist together in an E2F complex because antibodies against E2F-1 supershift complexes which also contain DP-1. This is reminiscent of the situation that exists in other transcription factor activities, for example AP-1, where very different proteins interact through related domains. It is, however, believed that there is more than one partner for DP-1 because although DP-1 is present in all DRTF1/E2F complexes that form on the E2F binding site, antibody supershift experiments indicate that E2F-1 is not; perhaps other E2F-1-like polypeptides exist together with DP-1 in these complexes.

Several lines of evidence suggest that the cellular transcription factor DRTF1/E2F plays an important role in regulating the cell cycle of mammalian cells. For example, DRTF1/E2F DNA binding activity is periodically induced during cell cycle progression, peaking during S phase (Mudryj et al., 1992; Shirodkar et al., 1992), and negatively regulated during differentiation (La Thangue & Rigby, 1987). This binding activity correlates with the transcriptional activity of certain genes that are necessary for cellular proliferation, such as DHFR, DNA polymerase α and $p34^{cdc2}$, which contain DRTF1/E2F binding sites in their promoters (Black & Azizkhan, 1989; Means et al., 1992; Dalton, 1992). Furthermore, the retinoblastoma tumour suppressor gene product, which negatively regulates cell cycle progression from G1 into S phase and is frequently mutated in tumour cells, binds to DRTF1/E2F (Bandara and La Thangue, 1991; Chellapan et al., 1991). The functional consequence of this interaction is that pRb prevents DRTF1/E2F from activating transcription (Zamanian and La Thangue, 1992). Several other molecules that are implicated in cell cycle control, such as Rb-related p107, cyclins A and E, and $p33^{cdk2}$ also associate with DRTF1/E2F during cell cycle progression (Bandara et al., 1991, 1992; Mudryj et al., 1991; Devoto et al., 1992; Lees et al., 1992). Taken together, these observations suggest that DRTF1/E2F integrates cell cycle events with the transcription apparatus, ensuring that the cell makes the appropriate changes in gene expression at the correct time during cell cycle progression.

Further evidence for the importance of DRTF1/E2F has come from studies on the mechanism of action of viral oncoproteins. Thus, certain oncoproteins, such as adenovirus Ela, SV40 large T antigen and human papilloma virus E7 regulate the activity of DRTF1/E2F by sequestering pRb and the other associated proteins, converting it from a transcriptionally inactive to an active form (Zamanian and L Thangue, 1992; Hiebert et al., 1992; Zamanian and La Thangue, 1993). Because this effect requires regions in these viral oncoproteins previously shown to be necessary for cellular immortalization and transformation (Bandara and La Thangue, 1991; Zamanian and La Thangue, 1993), it is likely that DRTF1/E2F plays an important role in these processes.

Although progress has been made in identifying the cellular proteins that interact with DRTF1/E2F, relatively little was, until recently, known about its molecular details. Two distinct polypeptides which are both DNA binding components of DRTF1/E2F have now been molecularly characterised. The first, referred to as E2F-1, was isolated through its ability to directly bind to pRb, which it does through a C-terminal region (Helin et al., 1992; Kaelin et al., 1992). In contrast, DP-1 was defined as a component of DRTF1/E2F DNA binding activity after biochemically purifying DRTF1 from F9 embryonal carcinoma (EC) stem cells, a cell system in which DRTF1/E2F is down-regulated during the differentiation process (La Thangue and Rigby, 1987; La Thangue et al., 1990). cDNAs that encode DP-1 were isolated after obtaining amino acid sequence from affinity purified DP-1 (Girling et al., 1993).

Both E2F-1 and DP-1 contain a region that allows each polypeptide to bind in a sequence-specific fashion as a homodimer to the E2F motif (Helin et al., 1992; Kaelin et al., 1992; Girling et al., 1993). Although the DNA binding domains are not closely related to any previously defined DNA binding structure they are, nevertheless, distantly related to the DNA binding domains in some yeast cell cycle-regulating transcription factors (La Thangue and Taylor, 1993). The functional relationship between DP-1 and E2F-1 has, however, remained unclear. In this study, we show that DP-1 and E2F-1 exist as a complex in vivo which recognises the E2F binding site. Moreover, in vitro assays demonstrate that DP-1 and E2F-1 bind efficiently and preferentially as a complex to the E2F site, an interaction which requires the region of similarity between the two proteins. Furthermore, reconstructing DRTF1/E2F in Drosophila and yeast cells suggests that DP-1 and E2F-1 interact synergistically in E2F site-dependent transcriptional activation. These data indicate that DP-1 and E2F-1 can functionally interact and that such an interaction is likely to be physiologically relevant in mammalian cells.

DP-b 1 and E2F-1 Exist as a Complex in HeLa Cells

DP-1 is a component of DRTF1-E2F which is present in murine developmentally regulated and cell cycle regulated DRTF1/E2F complexes and thus is likely to be a general component of DRTF1/E2F DNA binding activates. Furthermore, DP-1 is the product of a conserved gene since it has been observed by the present inventor that a closely related protein is expressed in amphibians and Drosophila. DP-1 thus appears to be a frequent and evolutionarily conserved DNA binding component of DRTF1/E2F. E2F-1, which was isolated through its ability to bind directly to pRb, also interacts in a sequence-specific fashion with the E2F site (Helin et al., 1992; Kaelin et al., 1992). Both proteins contain a small region of similarity that overlaps domains previously shown to be necessary for sequence-specific DNA binding activity (Girling et al., 1992).

Figure 6A:
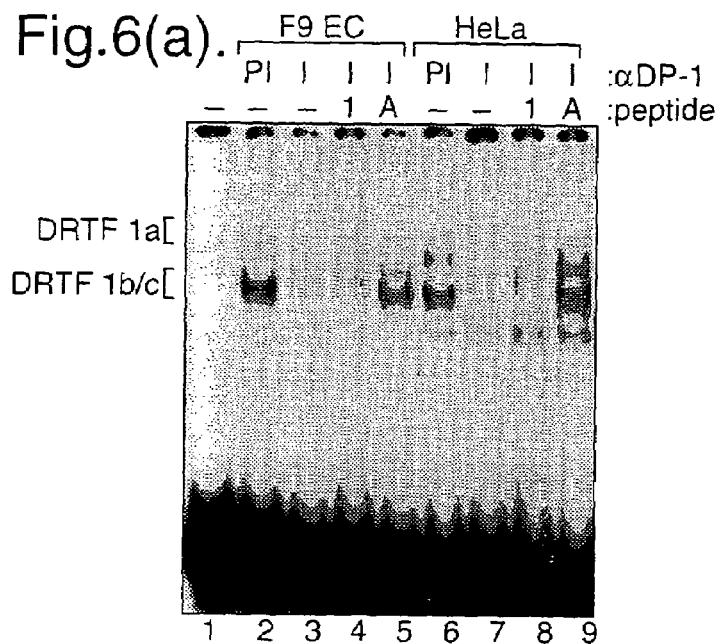
FIG. 6 shows that DP-1 and E2F-1 exist in the same protein complex in vivo.
Figure 6B:
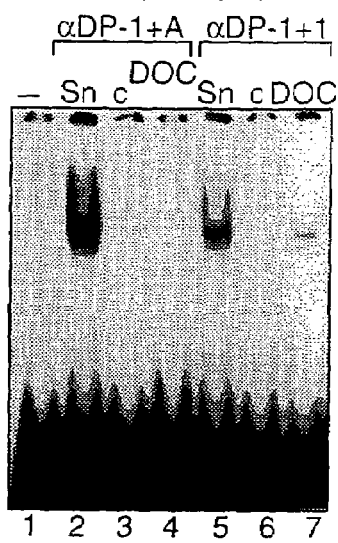
Figure 6C:
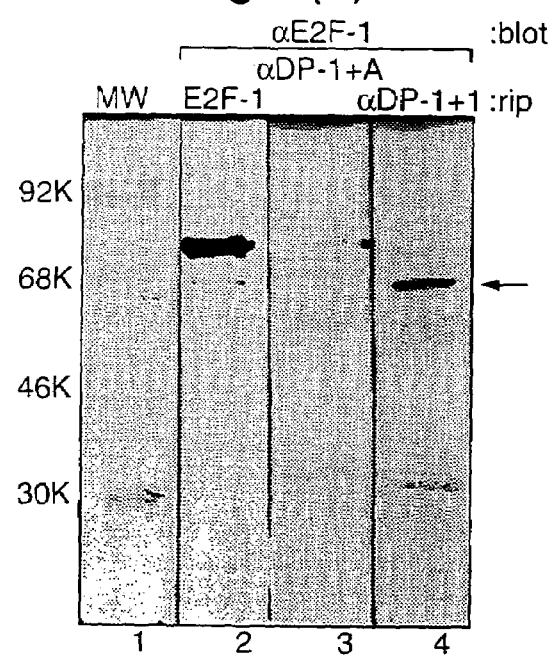

It was assessed whether DP-1 and E2F-1 exist as a complex in HeLa cell extracts using antibodies that specifically recognise each protein. Initially, we determine by gel retardation whether DP-1 is a component of HeLa cell DRTF1/E2F. Thus, as in F9 embryonal carcinoma (EC) cell extracts, anti-DP-1 peptide antiserum disrupted HeLa cell DRTF1/E2F in a specific fashion since its effects were competed by including in the binding reaction the homologous, but not an unrelated, peptide (FIG. 6a, compare tracks 2 through 5 with 6 through 9). Anti-DP-1 antiserum was used to immunoprecipitate DRTF1/E2F from HeLa cell extracts, the immunoprecipitate subsequently being released and then immuneblotted with an anti-E2F-1 monoclonal antibody. The DRTF1/E2F DNA binding activity immunoprecipitated by anti-DP-1 (FIG. 6b, compare tracks 4 and 7) contained the E2F-1 protein because immunoblotting the immunoprecipitates with an anti-E2F-1 monoclonal antibody revealed a polypeptide with the molecular weight expected for E2F-1 (FIG. 6c, track 4, indicated by arrow). The presence of E2F-1 was dependent upon the anti-DP-1 activity since it was not present when the immunoprecipitation was performed in the presence of the homologous peptide (FIG. 6c, compare tracks 3 and 4). Thus, DP-1 and E2F-1 exist as a complex in HeLa cell extracts.

DP-1 and E2F-1 Interact in vitro in a DNA Binding Heterodimer

Figure 7A:
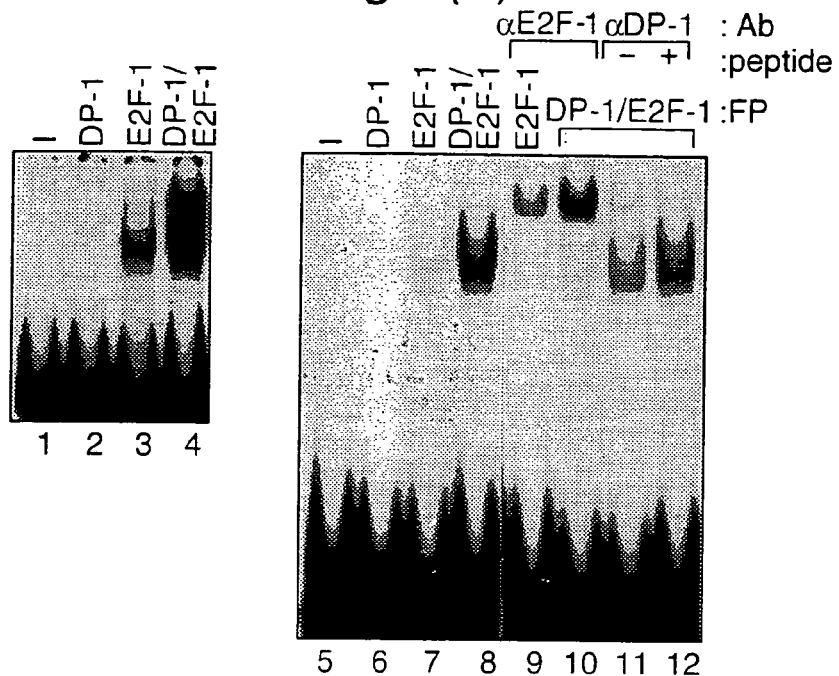
FIG. 7 shows that DP-1 and E2F-1 bind to the E2F site as a complex.

Both DP-1 and E2F-1 contain sequence-specific DNA binding domains, located in similar positions of each protein (between amino acid residue 84 and 204 in DP-1, and 89 to 191 in E2F-1; Girling et al., 1993), which contain a region of similarity that extends outside of the DNA binding domain, to amino acid residue 249 in DP-1. In agreement with previous studies (Helin et al., 1992; Kaelin et al., 1992; Girling et al., 1993) both DP-1 and E2F-1 along were able to bind to the E2F site, either in the context of the adenovirus E2A promoter (FIG. 7a, tracks 2 and 3) or as a single E2F site (which was apparent on increased exposure of FIG. 7a, track 6; data not shown). The DNA binding activity of DP-1 was somewhat less than that of E2F-1, the reasons for which are currently unclear. However, when both proteins were present in the same binding reaction, increased E2F site DNA binding activity was apparent (FIG. 7a, compare tracks 2 and 3 with 4, and 6 and 7 with 8). The DNA binding activity was much greater than that expected from an additive effect of the two DNA binding activities, indicating that together DP-1 and E2F-1 recognise the E2F site synergistically.

The presence of both DP-1 and E2F-1 in the DNA binding complex was confirmed using antisera specific for either protein. An anti-E2F-1 peptide antiserum supershifted the DNA binding complex (FIG. 7a, compare track 8 with 10), whereas the anti-DP-1 peptide antiserum inhibited the DNA binding activity (FIG. 7a, compare track 11 and 12). However, the effect of the anti-DP-1 antiserum was less dramatic, the reasons for which are unclear, but may be related to the availability of the epitope which, for this antibody, is located close to the DNA binding domain of DP-1 (Girling et al., 1993).

Figure 7B:
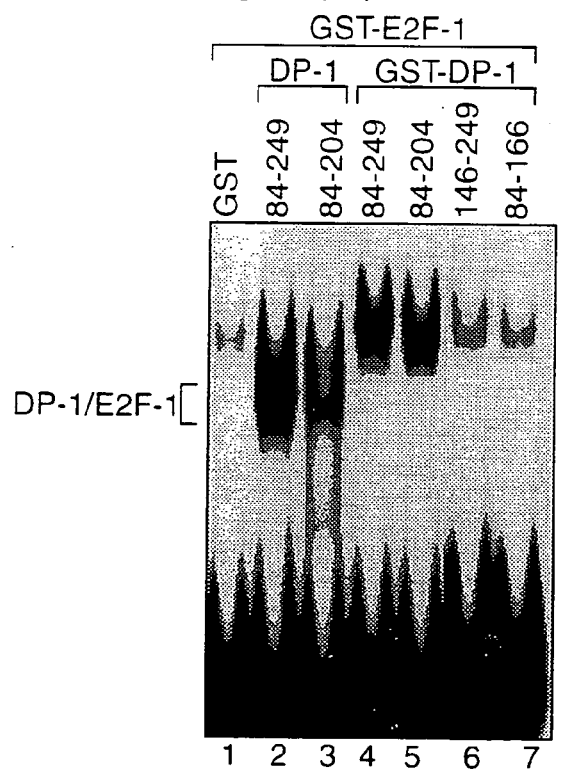

This assay was used to determine the regions in DP-1 which are necessary to produce a DNA binding complex with E2F-1. Thus, various derivatives of DP-1 were expressed as GST fusion proteins, cleaved with thrombin, and then assessed for any interaction with E2F-1. Since these derivatives of DP-1 were truncated versions of the wild-type protein, any of them which was able to interact with E2F-1 to produce functional DNA binding activity should result in a smaller and hence faster migrating DNA binding complex. Moreover, if only one faster migrating complex were apparent, a heterodimer of the two proteins would be the most likely explanation. Indeed, when either DP-1$^{84-249}$ or DP-1$^{84-204}$ were mixed with E2F-1 (GST-E2F-1$^{89-437}$), a faster migrating DNA binding complex was formed relative to E2F-1 alone (FIG. 7b, compare track 1 with 2 and 3) or E2F-1/DP-1 (FIG. 7a) indicating that these two derivatives of DP-1 were able to interact with E2F-1 and that they were likely to form a heterodimer. Again, the DNA binding activity of the E2F-1/DP-1$^{84-249}$ complex was greater than that for E2F-1 alone (FIG. 7b, compare track 1 with 2 and 3) or DP-1$^{84-249}$ which had low DNA binding activity in the conditions employed in this assay (data not shown) but nevertheless can specifically recognise the E2F site (Girling et al., 1993). The DNA binding activity of the E2F-1/DP-1$^{84-204}$ reaction was less than E2F-1/DP-1$^{84-249}$ indicating that the region of DP-1 between amino acid residue 204 and 249, which shows significant similarity to E2F-1 (Girling et al., 1993), also influences DNA binding activity. The synergistic DNA binding effects of DP-1$^{84-249}$ and DP-1$^{84-204}$ were also apparent when the uncleaved GST fusion proteins were mixed with E2F-1 although, because of their increased size, a faster migrating DNA binding complex did not occur (FIG. 7b, compare track 1 with 4 and 5). Further deletion of this region, either from the N-(DP-1$^{146-249}$) or C-(DP-1$^{84-166}$) terminus yielded derivatives of DP-1 that failed to form a DNA binding complex with E2F-1 either as GST fusion proteins (FIG. 7b, compare track 1 with 6 and 7) or after cleavage (data not shown), indicating that DP-1$^{84-204}$ is the minimal region so far defined which is capable of producing a DNA binding complex with E2F-1.

Figure 7C:
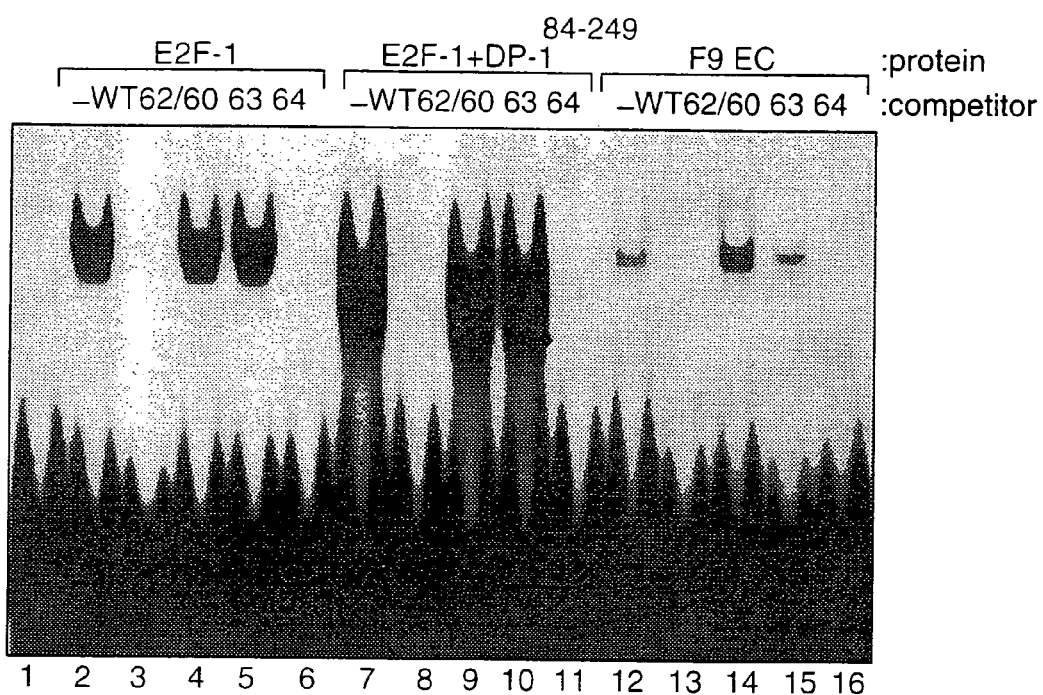

Analysis of the DNA binding specificity of the E2F-1/DP-1$^{84-249}$ complex with a panel of binding sites derived from the adenovirus E2A promoter distal E2F site (La Thangue et al., 1990; Shivji and La Thangue, 1991) indicated that it was very similar to that for E2F-1 alone (FIG. 7c, compare tracks 3 through 6 with 8 through 11) and, furthermore, the DRTF1/E2F site DNA binding activity defined in F9 EC cell extracts (FIG. 7c, compare tracks 13 through 16).

Figure 7D:
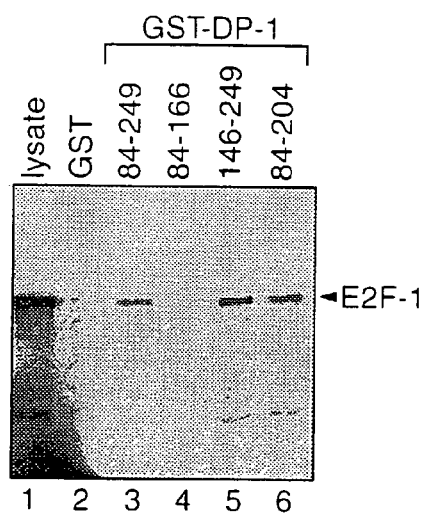
Figure 7E:
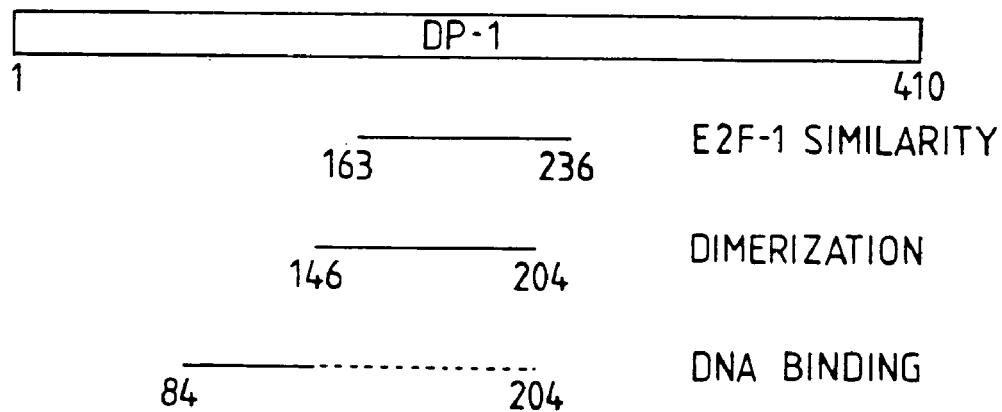

To characterise further the interaction between DP-1 and E2F-1 we employed an assay in which in vitro transcribed and translated E2F-1 polypeptide could bind to DP-1GST fusion proteins. The ability of E2F-1 to interact with DP-1 was assessed after collecting the GST-fusion protein with glutathione-agarose beads and subsequently releasing the bound E2F-1 polypeptide. Both DP-1$^{84-249}$ could interact with E2F-1 since the amount of E2F-1 bound to GST-DP-1$^{84-249}$ and GST-DP-1$^{84-204}$ was significantly greater than that bound by the GST beads along (FIG. 7d, compare track 2 to 3 and 6), consistent with their ability to form a DNA binding heteromer (FIG. 7b). DP-1$^{146-249}$ also bound to E2F-1 whereas DP-1$^{84-166}$ failed to do so (FIG. 7d, compare tracks 2 to 4 and 5). DP-1$^{146-249}$ therefore contains a domain, which based on the earlier results is likely to be a dimerization domain, that allows it to interact with E2F-1 but lacks sufficient amino acid sequence for the heteromer to bind to DNA. The additional information in DP-1$^{84-249}$ is necessary for the complex to bind to DNA. These data therefore suggest that the region of DP-1 which is similar to E2F-1 (amino acid 163 to 236) contains a dimerization domain, and that additional N-terminal sequence is necessary for DNA binding activity. A summary of these data is presented in FIG. 7e.

DP-1 and E2F-1 Interact in Yeast Cells

Figure 8:
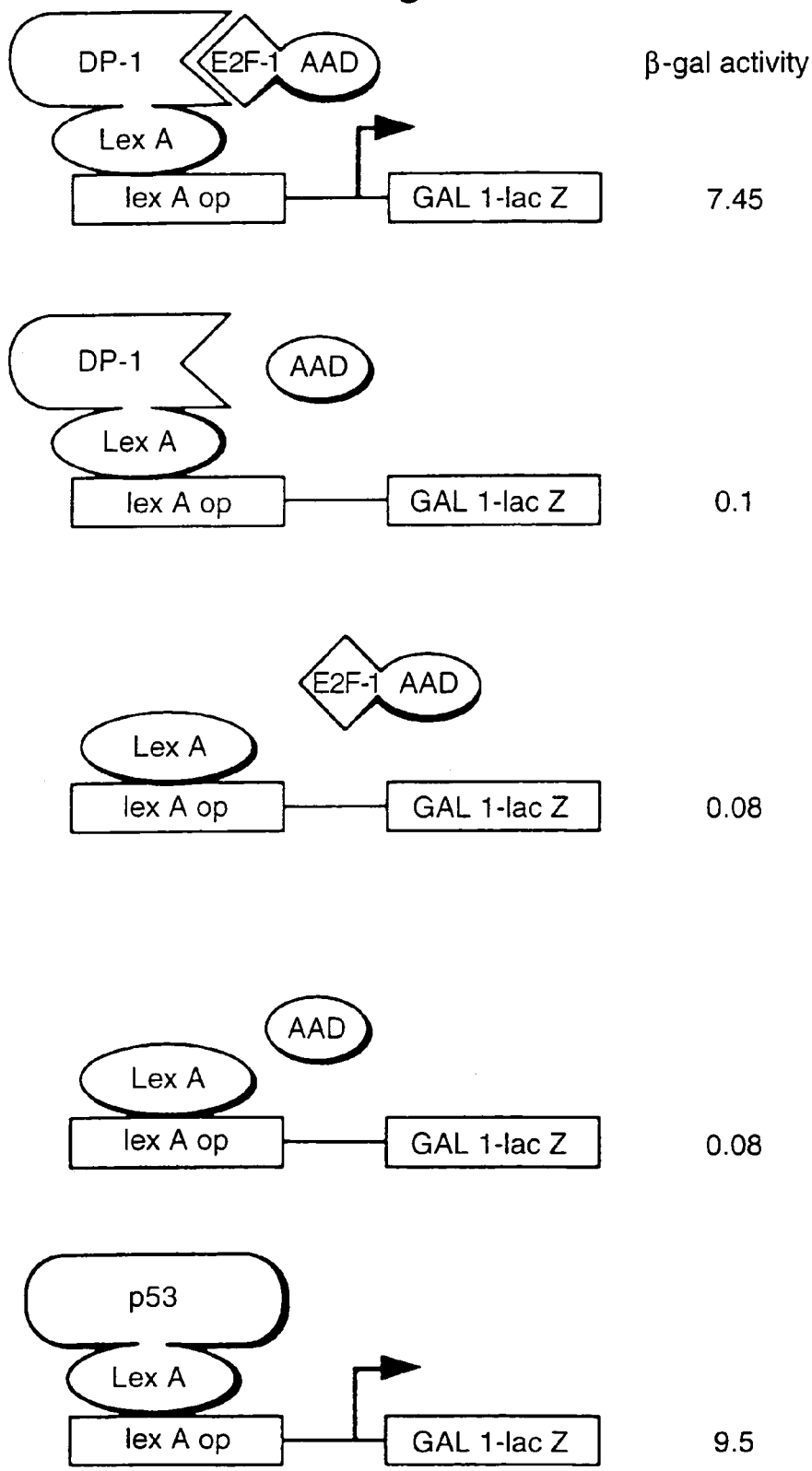
FIG. 8 shows the interaction of DP-1 and E2F-1 in yeast cells.

To determine if DP-1 and E2F-1 interact directly in vivo we adapted a previously described assay system in yeast cells (Fields and Song, 1989) which utilised expression vectors that synthesise two hybrid proteins, one derived from DP-1 and the other from E2F-1. In the first, the DP-1 coding sequence was fused to the DNA binding domain of the bacterial LexA protein, to make pLEX.DP-1 and in the second, pGAD.E2F-1, the E2F-1 coding sequence was fused with the acidic transcriptional activation domain (AAD) of the yeast Gal4 protein. pLEX.DP-1 failed to activate a reporter construct driven by a LexA binding site, whereas a hybrid protein that contained the trans activation domain taken from the p53 protein could (FIG. 8). However, when pLEX.DP-1 and pGAD.E2F-1 were expressed together, the transcriptional activity of the LexA reporter construct was increased considerably (about 75-fold) relative to its activity when either pLEX.DP-1 or pGAD.E2F-1 were expressed alone (FIG. 8). This result, combined with the earlier studies presented in this paper, strongly suggest that DP-1 and E2F-1 interact directly in vivo.

DP-1 Regulates E2F Site-dependent Transcription in vivo

Increasing the levels of the DP-1 protein in a variety of mammalian cells (for example, F9 EC, SAOS-2 and 3T3) and growth conditions failed to significantly stimulate the transcriptional activity of an E2F site-dependent reporter (data not shown). In order to assess if DP-1 and E2F-1 functionally interact we therefore had to take an alternative approaches.

(a) Drosophila Assay

Figure 9A:
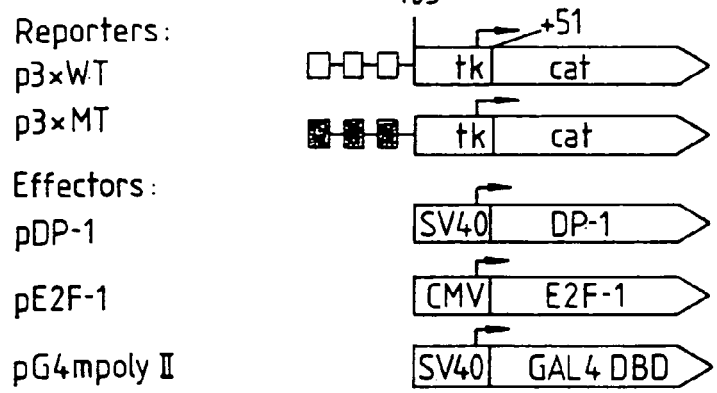
FIG. 9 shows there is functional synergy between DP-1 and E2F-1 in *Drosophila* cells.
Figure 9B:
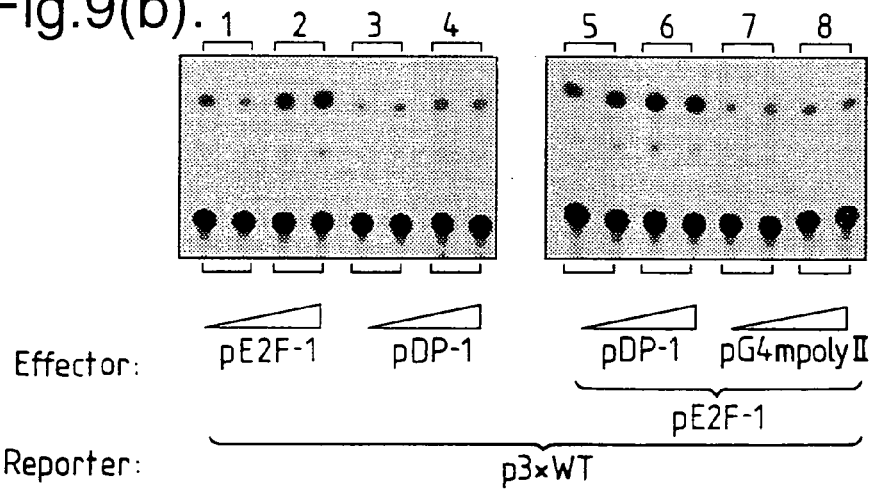
Figure 9C:
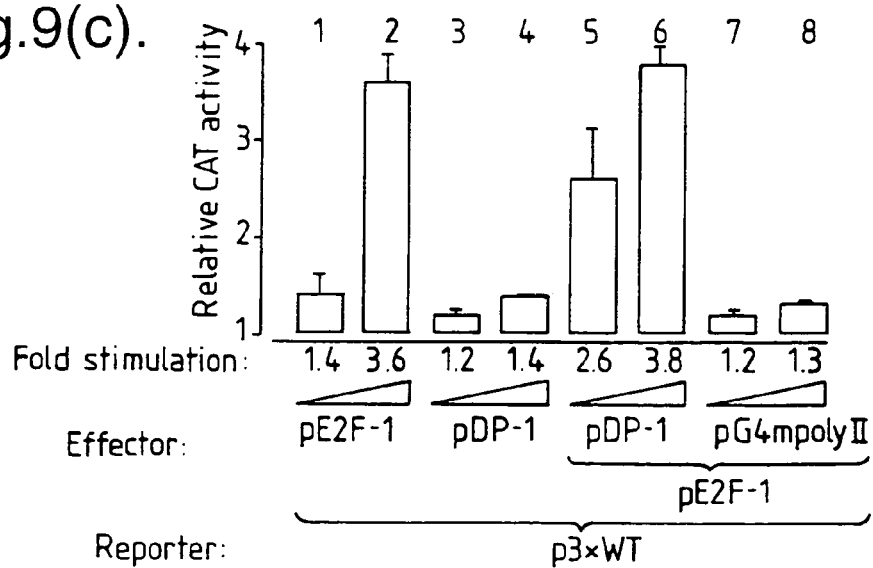

A first approach involved developing the appropriate assay in Drosophila SL2 cells, a cell system which has been used previously to study the activity of mammalian transcription factors (Courey and Tjian, 1988). These cells were particularly appropriate for this analysis because the endogenous E2F site DNA binding activity is very low when assayed by gel retardation (data not shown). In order to assess the functional interaction of DP-1 and E2F-1, we determined the effects of each protein alone and when expressed together on the transcriptional activity of p3xWT, a reporter construct driven by three E2F sites (FIG. 9a; Zamanian and La Thangue, 1991). Thus, E2F-1 was able to activate p3xWT in a dose-dependent fashion (FIGS. 9b and c, compare lanes 1 and 2) whereas DP-1 failed to do so (FIGS. 9b and c, compare lanes 3 and 4), results which are similar to the behavior of E2F-1 and DP-1 in mammalian cells (Helin et al., 1992; Kaelin et al., 1993; and data not shown). However when DP-1 and E2F-1 were expressed together much greater E2F site-dependent transcriptional activation was apparent relative to either alone (FIGS. 9b and c, compare lanes 1, 3 and 5). Moreover, this synergistic effect was titratable because increasing the level of DP-1 produced more E2F site-dependent transcription (FIGS. 9b and c, compare lanes 1, 5 and 6) and specific since co-expression of an unrelated DNA binding, derived from the Gal4 protein, did not produce any significant effects (FIGS. 9b and c, compare lanes 5 and 6 with 7 and 8). Moreover, similar expreriments performed with p3xMT indicated that this activation was specific for the wild-type E2F site (data not shown). It therefore appears that DP-1 and E2F-1 functionally interact in E2F site-dependent transcription and that this interaction is synergistic.

(b) F9 EC Cell Assay

Figures 10A, 10B:
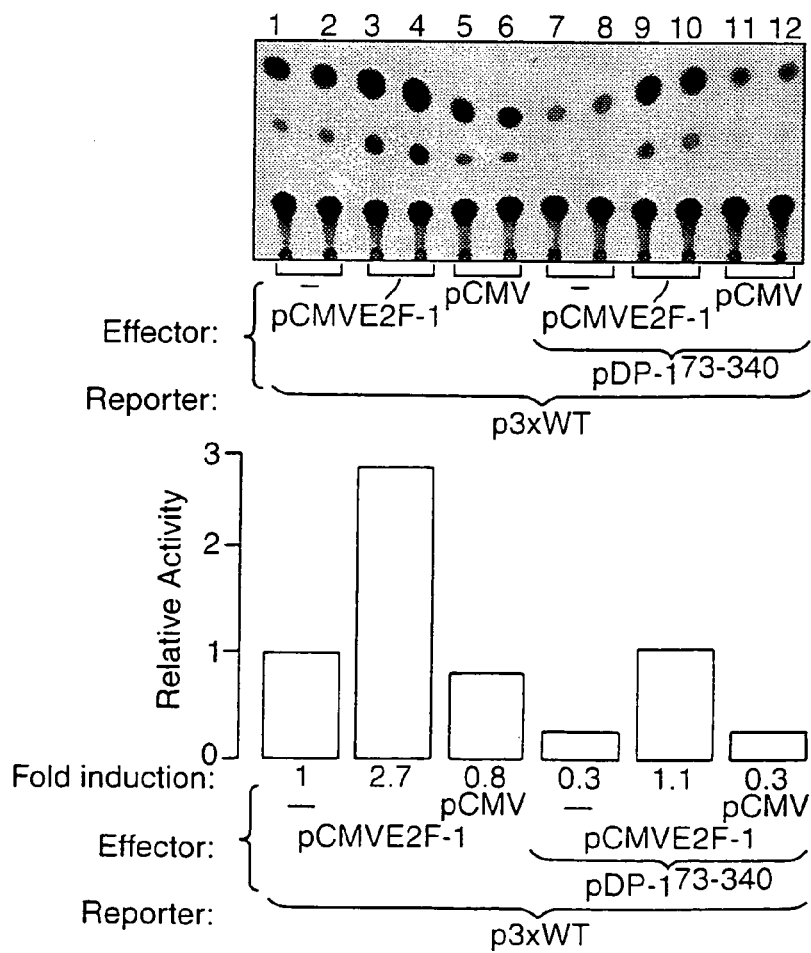
FIG. 10 shows DP-1 contributes to E2F site-dependent transcription in F9 EC cells.

In an alternative approach a "dominant negative" derivative of DP-1 was designed which could cripple the endogenous DRTF1/E2F transcriptional activity. DP-1$^{73-340}$ was prepared which lacks amino acid sequence from both the N and C-terminal region. Thus, when DP-1$^{73-340}$ was expressed in F9 EC cell, which contain high levels of E2F site-dependent transcriptional activity (Zammanian and La Thangue, 1992, a reduction in the activity of p3xWT was apparent (FIG. 10c, compare tracks 1 and 2 to 7 and 8, quantitated at the bottom of the figure); this effect was specific for the wild type E2F site because the activity of either the mutant E2F site reporter p3xMT or pCMVcat was not affected. Based on the earlier results, a potential explanation for the effect of DP-1$^{73-340}$ was that it sequestered E2F-1, to form a heteromer that was not capable of activating transcription, thus limiting the amount of available E2F-1. When E2F-1 was expressed in the presence of DP-1$^{73-340}$, it overcame the "dominant negative" activity and partially restored E2F site-dependent transcriptional activity (FIG. 10, compare tracks 7 and 8 to 9 and 10). The ability of E2F-1 to rescue E2F transcriptional activity is consistent with the idea that DP-1$^{73-340}$ sequesters E2F-1 into an inactive transcription complex and is compatible with the idea that an interaction between DP-1 and E2F-1 occurs in mammalian cells.

DP-1 and E2F-1 Activate E2F Site-dependent Transcription Yeast Cells

Figure 11A:
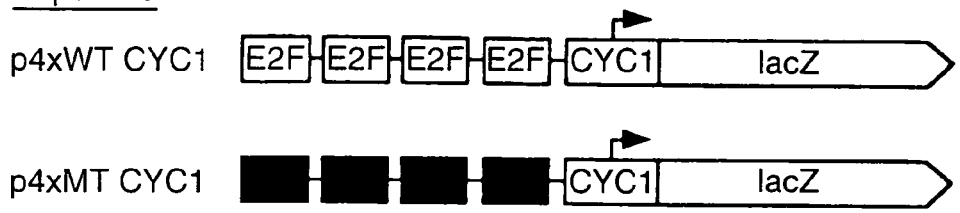
FIG. 11 shows DP-1 and E2F-1 activate E2F site-dependent transcription in yeast cells.
Figure 11A:
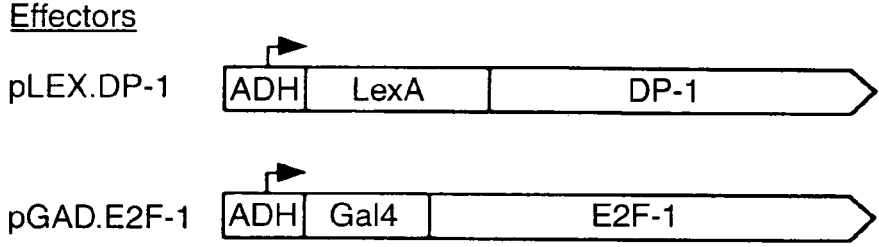
Figure 11B:
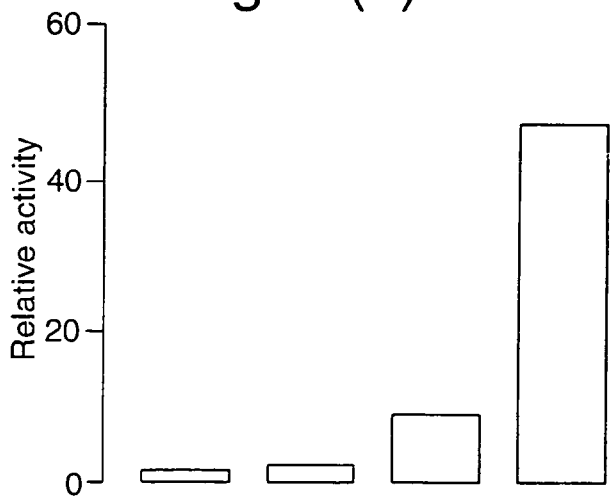

DP-1 and E2F-1 were then assessed to determine if they can functionally interact in E2F site-dependent transcription in yeast cells. For this, constructs in which the yeast cyc1 promoter was driven by E2F binding sites taken from the adenovirus E2A promoter were used. In p4xWT CYC1, four E2F binding sites drive the cyc1 promoter (FIG. 11a), activating transcription about 12-fold above the activity of p4xMT CYC1 (data not shown). This transcriptional activity could be stimulated further upon introduction of the E2F-1 expression vector, pGAD.E2F-1. Thus, pGAD.E2F-1 increased the transcriptional activity of p4xWT CYC1 about 10-fold, compared to the small effect that the DP-1 expression vector, pLEX.DP-1, had on the same reporter construct (FIG. 11b). However, when E2F-1 and DP-1 were expressed together, the activity of p4xWT CYC1 was even greater, and usually about 50-fold above basal p4xWT CYC1 activity (FIG. 5b); the activity of p4xMT CYC1 was not significantly affected by either the E2F-1 or DP-1 expression vector (data not shown). This shows that DP-1 and E2F-1 activate E2F site-dependent transcription more efficiently when present together than either does alone, suggesting again that DP-1 and E2F-1 interact synergistically in E2F site-dependent transcriptional activation.

DP-1 and E2F-1 Interact in Mammalian Cells

Previous studies have indicated that DP-1 is a universal component of DRTF1/E2F DNA binding activity in F9 EC cells because all the DNA binding complexes that occur on the E2F site are disrupted by anti-DP-1 antibodies (Girling et al., 1993). The same situation exists in HeLa cell extracts where all the DRFT1/E2F DNA binding complexes are affected by anti-DP-1 antibodies (FIG. 6a). Based on these observations, and combined with studies performed in other cell types (Bandara et al., in preparation), we believe that DP-1 is a frequent component of transcription factor DRTF1/E2F.

In the light of these observations, we were interested to determine if DP-1 can interact with the other E2F site DNA binding protein, E2F-1 (Helin et al., 1992; Kaelin et al., 1992) and, furthermore, establish whether such an interaction occurs in physiological conditions. Our results indicate that DP-1 and E2F-1 exist as a complex in HeLa cell extracts, and thus imply that at least a proportion of the total DRTF1/E2F DNA binding activity is likely to be heteromeric complex involving DP-1 and E2F-1. It is unclear, at the moment, just how much of the DRTF1/E2F DNA binding activity is a complex of DP-1 and E2F-1 because our attempts to use anti-E2F-1 antibodies to affect the DNA binding activity in gel retardation assays have been unsuccessful (data not shown). Also, we cannot rule out that other proteins bind to DP-1, in the place of E2F-1. In fact, this would seem a likely possibility because several polypeptides in affinity purified DRTF1/E2F with distinct molecular weights (from 45 to 55,000) are capable of specifically binding to the E2F site (Shivji and La Thangue, 1991; Girling et al., 1993).

A Physical Interaction Between DP-1 and E2F-1 in vitro and in Yeast Cells

We established that DP-1 and E2F-1 can directly interact by studying their DNA binding properties in gel retardation assays. DP-1 and E2F-1 formed a heteromeric DNA binding complex with exactly the same DNA binding specificity as that possessed by DRTF1/E2F in crude cell extracts (La Thangue et al., 1990). Moreover, it was apparent that the DNA binding activity of the heteromer was considerably greater than for E2F-1 or DP-1 alone, suggesting that DP-1 and E2F-1 interact synergistically. A molecular analysis of the region in DF-1 which was necessary to form a DNA binding complex with E2F-1 indicated that the region of similarity between the two proteins, together with an additional N-terminal domain; was required. The region of similarity allowed DP-1 and E2F-1 to bind to each other and thus is likely to constitute a dimerization domain.

We confirmed these observations in yeast cells using an assay which makes use of the modular organisation of transcription factors (Fields and Song, 1989). Thus, DP-1 was fused to the bacterial LexA DNA binding domain and, in a separate molecule, E2F-1 to the acidic transcriptional activation domain of the yeast Gal4 protein. In this assay, a functional activation domain is recruited to the LexA-dependent promoter only if there is a physical interaction between the two hybrid proteins. When the two hybrid proteins were expressed together there was strong activation of the LexA-dependent reporter. Thus, DP-1 and E2F-1 are able to physically interact in yeast cells. Moreover, this result indicates that they are able to do so in the absence of DNA binding since the DNA binding specificity was provided by LexA and thus took place independently of the E2F binding site.

Transcriptional Synergy by DP-1 and E2F-1 in vivo

We addressed the functional consequences of the interaction between DP-1 and E2F-1 for E2F site-dependent transcription in both *Drosophila* and yeast cells. We took this approach because our attempts to activate transcription by introducing wild-type DP-1 into mammalian cells have met with limited success, the reasons for which are unclear but may be related to the levels of endogenous DP-1 protein.

Both types of assay, whether performed in *Drosophila* or yeast cells, indicated that DP-1 and E2F-1 interact synergistically in E2F site-dependent transcription since when both proteins were expressed together transcriptional activation was more efficient than for either protein alone. A likely explanation for such an effect is that the DNA binding activity of the DP-1/E2F-1 heterodimer is more stable than either homodimer and thus transcriptional activation is more efficient. This idea would be entirely consistent with the in vitro DNA binding data presented earlier in this study which suggested that DP-1 and E2F-1 interact synergistically. We cannot, however, rule out other potential influences, such as activation of a cryptic transcriptional activation domain in the DP-1/E2F-1 heterodimer and, in fact, recent experiments have suggested that such a possibility is likely to be correct (Zamanian and La Thangue, unpublished data).

In conclusion, we have demonstrated that DP-1 and E2F-1 interact in transcription factor DRTF1/E2F, to produce a DNA binding complex which is the preferred state over either homodimer. Since E2F-1 can bind to pRb (Helin et al., 1992; Kaelin et al., 1992) in such a complex it is likely that E2F-1 will provide an interface recognised by pRb, thus enabling the transcriptional activity of this particular E2F site DNA binding activity to be regulated by pRb. It is possible that other molecules heterodimerize with DP-1, in the place of (and perhaps related to) E2F-1, providing an interface recognised by other proteins which are known to interact with E2F/DRTF1, such as p107 (Zamanian and La Thangue, 1993), thus allowing these molecules also to regulate E2F site-dependent transcription. We suggest therefore that distinct heterodimers recognise the E2F site, with DP-1 as a common component, enabling different molecules, such as pRb and p107, to integrate their biological activities with the transcription apparatus and hence to regulate genes driven by E2F/DRTF1.

MATERIALS AND METHODS

Preparation of Cell Extracts, Gel Retardation and Immunochemical Techniques

Cell extracts were prepared as previously described (La Thangue et al., 1990). Gel retardation in F9 EC and HeLa cell extracts (about 6.0 µg) in the presence of anti-DP-1 was performed as previously described (Girling et al., 1993), and immunoprecipitation with anti-DP-1 from HeLa cell extracts was performed by standard procedures. The immunoprecipitates were treated with 1% DOC and 1.5% NP40 and the detergent released material assayed for DRTF1/E2F by gel retardation and the presence of E2F-1 by immunoblotting with the anti-E2F-1 monoclonal antibody SQ41 (Kaelin et al., 1992). The anti-DP-1 antibodies, anti-peptide A and anti-peptide 18, have been previously described (Girling et al., 1993). Rabbit anti-E2F-1 antiserum (antiserum 134) was raised against a peptide which represents E2F-1 amino acid sequence 315 to 323. The sequences of the binding sites used to assess DNA binding specificity were derived from the adenovirus E2A promoter (−71 to −50) and were as follows: WT; TAGTTTTCGCGCTTAAATTTGA (SEQ ID NO: 7); 62/60, TAGTTTTCGATATTAAATTTGA; (SEQ ID NO: 8); 63, TAGTTTTCTCGCTTAAATTTGA (SEQ ID NO: 9); 64, TAGTTTTAGCGCTTAAATTTGA (SEQ ID NO: 10). In FIG. 2a (tracks 1 to 4), the adenovirus E2A promoter (−96 to +68) was used; in all other cases, the distal E2F site in the E2A promoter (sequences −71 to −50) was used. About 100-fold excess of competing binding sites were used in the gel retardation assays.

Fusion Proteins and in vitro Translation

DP-1 and E2F-1 were expressed as, and released from, GST fusion proteins as previously described (Girling et al., 1993). About 100-fold excess of the competing binding sites were used in gel retardation assays, with the binding site taken from the adenovirus E2A promoter (−71 to −50). The wild-type E2F-1 coding sequence was transcribed and further translated using reticulocyte lysate (Promega) and radiolabelled with $^{35}$S methionine. In the dimerization assay (FIG. 2d), GST-DP-1 fusion protein was incubated with E2F-1 polypeptide for 30 min at 30° C., collected with glutathione-agarose (Sigma), and washed repeatedly with 0.1% NF40-in PBSA. Bound E2F-1 polypeptide was released by denaturation in SDS sample buffer and resolved in a 10% polyacrylamide gel.

Yeast Assays pBTM116 contains the complete LexA coding sequence (1–202) under the control of the yeast ADH1 promoter. pLEX.DP-1 carries the coding sequence for DP-1 (from amino acid 59 to the C-terminus) downstream of the LexA coding sequence in pBTM116. pBTM126 carries the wild-type murine p53 coding sequence (from amino acid 1 to 346) downstream of the LexA DNA binding domain. pGAD.L6 is a derivative of pGAD2F (Chien et al., 1991) containing the Gal4 transcription activating domain (from amino acid residue 768–881) under the control of yeast ADH1 promoter. pGAD.E2F-1 contains the entire E2F-1 coding sequence (from amino acid 1 to 437) downstream of the Gal4 activation domain. p4xWT CYC1 and p4xMT CYC1 were derived from pLGΔ178 (Guarente and Mason, 1983). The wild-type E2F site was taken from the −71 to −50 region of the adenovirus E2A promoter and the mutant site was mutated in nucleotides −62 to −60 (La Thangue et al., 1990). For the yeast interaction assay (FIG. 3), the indicated expression vectors were transformed into the yeast strain CTY10-5d (MATa ade2 trip1-901 leu2-3, 112 his3-200 gal4 gal80 URA3::lexAop-lacZ) which contains an integrated plasmid which carries 2 copies of a 78-bp oligonucleotide, each copy containing two colEl operators or four binding sites for LexA dimers upstream of the transcription start site of GAL1-lacZ. For the yeast E2F site-dependent transcription assay (FIG. 5), the yeast strain W3031a (MATa ade 2-100 tryp1-1 leu2-3 112 his3-11 ura3) was used carrying either p4xWT CYC1 or p4xMT CYC1 and was transformed with the indicated expression vectors. β-galactosidase activity of mid-long phase cultures was quantitated as described previously (Johnson et al., 1986). β-galactosidase activity was measured for at least three independent transformants.

Transfection of Drosophila Tissue Culture Cells

Reporter constructs were all derived from pBLcat2 and have been previously described (Zamanian and La Thangue, 1992). Open and solid boxes denote wild-type and mutant E2F binding sites, respectively. pDP-1 encodes a complete DP-1 protein, and pG4mpolyII the Gal4 DNA binding domain (Webster et al., 1989). pE2F-1 has been previous described as pCMV RBAP-1 (Kaelin et al., 1982). Cells were transfected by the calcium phosphate procedure and harvested 40 to 45 h later and for each transfection, pBluescript KS was included to maintain the final DNA concentration constant. All transfections included an internal control pCMV β-gal. The assay for CAT activity, correction for transfection efficiency and quantitation of TLC plates have been described previously (Zamanian and La Thangue, 1992).

Transfection of Mammalian Cells

Reporter constructs were all derived from pBLcat2 and have been previously described (Zamanian and La Thangue, 1992). Open and solid boxes denote wild-type and mutant E2F binding sites, respectively. The plasmid pDP-1$^{73-340}$ encodes a protein spanning amino acids 73 to 340 in the wild-type DP-1 sequence fused downstream of the Gal4 sequences in pG4MpolyII (Webster et al., 1989). pCMV E2F-1 has been previous described as pCMV RBAP-1 (Kaelin et al., 1982). Cultivation of F9 EC cells and their transfection have been previously described (Zamanian and La Thangue, 1992). For each transfection, pBluescript KS was included to maintain the final DNA concentration constant. All transfections included an internal control pCMV β-gal. The assay for CAT activity and quantitation of TLC plates have been described previously (Zamanian and La Thangue, 1992).

DETAILED DESCRIPTION OF THE DRAWINGS

FIG. 6

DP-1 and E2F-1 exist in the same protein complex in vivo.

a) DP-1 is in DRTF1/E2F DNA binding complexes formed in HeLa cell extracts: gel retardation was performed using F9 EC and HeLa whole cell extracts (in which DRTF1 resolves as three distinct complexes, a, b, and c; indicated in figure) with the E2F binding site taken from the adenovirus E2A promoter (nucleotides −71 to −50) in the presence of either preimmune (PI; tracks 2 and 6) or immune (I; tracks 3 to 5 and 7 to 9) anti-DP-1 (peptide A) antiserum with the addition of either unrelated peptide 1 (tracks 4 and 8) or peptide A (tracks 5 and 9). In both F9 EC and HeLa cell extracts, all the DRTF1/E2F DNA binding complexes were affected by the anti-DP-1 antibody.

b) Anti-DP-1 immunoprecipitates DRTF1/E2F DNA binding activity: immunoprecipitation was performed from HeLa cell extracts with anti-DP-1 in the presence of either homologous peptide A (tracks 2 to 4) or unrelated peptide 1 (tracks 5 to 7). The immunoprecipitates were treated with 1% deoxycholate (DOC) and 1.5% NP40, and the detergent-released material assayed for DRTF1/E2F DNA binding activity; the depleted HeLa cell extract is also indicated (Sn; tracks 2 and 5). No DNA binding activity was released in the absence of detergent (indicated by c; tracks 3 and 6).

c) Immunoblotting DP-1 immunoprecipitates with anti-E2F-1: anti-DP-1 immunoprecipitates performed in the presence of either peptide A (track 3) or peptide 1 (track 4) were immunoblotted with the anti-E2F-1 monoclonal antibody SQ41; the E2F-1 polypeptide, present in track 4, is indicated by the arrow. As a positive control, about 100 ng of the E2F-1 fusion protein, GST-E2F-1$^{89-437}$, was immunoblotted in track 2. Track 1 shows standard molecular weights.

FIG. 7

DP-1 and E2F-1 bind to the E2F site as a complex.

a) DP-1 and E2F-1 interact synergistically in DNA binding to the E2F site: GST-DP-1$^{59-410}$ (about 25 ng) or GST-E2F-1$^{89-437}$ (about 50 ng) were assayed either along (tracks 2, 2, 6 and 7) or together (tracks 4 and 8) for binding to the adenovirus E2A promoter (tracks 1 to 4) or the distal E2F site taken from the E2A promoter (tracks 5 to 8); tracks 1 and 5 show the binding sites alone. Note that a DNA binding complex was apparent in track 6 upon increased exposure (data not shown). The E2F site-specificity of the complexes was confirmed by performing the appropriate competition experiments (data not shown). The effect of anti-E2F-1 (tracks 9 and 10) or anti-DP-1 (tracks 11 and 12; anti-peptide 18; Girling et al., 1993) was assessed on GST-E2F-1$^{89-437}$ alone (track 9) or GST-E2F-1$^{89-437}$ and GST-DP-1$^{59-410}$ together (tracks 10, 11 and 12). In addition, the reactions in tracks 11 and 12 contain either an unrelated (track 11) or the homologous (peptide 18; track 12) peptides.

b) DP-1 and E2F-1 form DNA binding heteromers: GST-E2F-1$^{89-437}$ (about 50 ng) was incubated with control GST fusion protein (about 300 ng; track 1) or DP-1$^{84-249}$ or DP-1$^{84-204}$ (about 150 ng, released after cleavage with thrombin; tracks 2 and 3), GST-DP-1$^{84-249}$, GST-DP-1$^{84-204}$, GST-DP-1$^{146-249}$ or GST-DP-1$^{84-166}$ (about 300 ng, without cleavage; tracks 4, 5, 6 and 7).

c) Sequence specificity of the E2F-1$^{89-437}$/DP-1$^{84-249}$ heteromer: the DNA sequence specificity of complexes formed by either GST-E2F-1$^{89-437}$ (50 ng; tracks 2 to 6) or GST-E2F-1$^{89-437}$ with DP-1$^{84-249}$ (50 ng and 150 ng respectively; tracks 7 to 11) was determined by competing with the wild-type or mutated derivatives of the distal E2F site from the adenovirus E2A promoter (about 100-fold molar excess of the binding sites indicated). For comparison, a similar experiment is shown in an F9 EC cell extract (track 12 to 16). Both mono- and heteromeric DNA binding complexes had very similar sequence specificities to F9 EC cell DRTF1/E2F. Track 1 shows the probe alone. Details of the competing binding sites are given in Materials and Methods.

d) DP-1 contains a dimerization domain: the indicated regions of DP-1 were expressed as GST fusion proteins (tracks 3 to 6) and about 2 µg incubated with 5 µl of a reticulocyte lysate containing translated wild-type E2F-1$^{1-437}$. GST fusion proteins, or GST protein along (track 2), were collected with glutathione-agarose beads and bound E2F-1 polypeptide released. Track 1 shows the lysate with the E2F-1 polypeptide. Note that DP-1$^{146-249}$ binds to E2F-1.

e) Summary of the data and molecular properties of DP-1. The C-terminal border of the DNA binding domain, which is known to lie within the region indicated by the broken line, has not been defined.

FIG. 8

DP-1 and E2F-1 interact in yeast cells

Summary of results. Details of the expression vectors and reporter construct are described above.

FIG. 9

Functional synergy between DP-b 1 and E2F-1 in *Drosophila* SL2 cells.

a) Summary of constructs: p3xWT and p3xMT have been previously described (Zamanaian and La Thangue, 1992). pDP-1 and pE2F-1 contain full length proteins, and pG4MpolyII the Gal4 DNA binding domain.

b) and c) SL2 cells were transfected with p3xWT and the indicated expression vectors. The amounts of expression vector in each treatment were as follows: 50 ng (lanes 1, 5, 6, 7 and 8) or 500 ng (lane 2) for E2F-1, 5 µg (lanes 3 and 5) or 10 µg (lanes 4 and 6) for DP-1, and 3.7 µg (lane 7) or 7.0 µg (lane 8) for pG4Mpoly II. All values are expressed relative to p3xWT alone which was given an arbitrary value of 1.0, and are representative of at least three separate experiments. b) shows an example of the crude data which is quantitatively represented in c).

FIG. 10

DP-1 contributes to E2F site dependent transcription in F9 EC cells.

a) Summary of constructs b) F9 cells were transfected with p3xWT and the indicated expression vectors. All treatments were performed in duplicate and corrected for transfection efficiency. All values are expressed relative to the activity of p3xWT alone which was given an arbitrary value of 1.0, and are representative of at least three separate experiments. Note that DP-1$^{73-340}$ cripples the endogenous DRTF1/E2F activity and that E2F-1 can rescue this effect. The data are represented graphically at the bottom of the figure.

FIG. 11

DP-1 and E2F-1 activate E2F site-dependent transcription in yeast cells.

a) Summary of constructs.

b) β-galactosidase activity was measured in *S. cerevisiae* strain W3031a carrying p4xWT CYC1 and the indicated effector expression vector. All values are expressed relative to the activity of p4xWT CYC1 which was given an arbitrary value of 1.0 and are representative of at least three separate experiments.

REFERENCES FOR SECTION B

Bandara, L. R. and La Thangue, N. B. (1991) *Nature*, 351, 494–497.

Bandara, L. R., Adamczewski, J. P., Hunt, T. and La Thangue, N. B. (1991) *Nature*, 352, 249–251.

Bandara, L. R., Adamczewski, J. P., Poon, R. C. Y., Zamanian, M., Hunt, T. and La Thangue, N. B. (1992) *J. Cell. Science*, 16, 77–85.

Blake, M. C. and Azizkhan, J. C. (1989) *Mol. Cell. Biol.*, 9, 4994–5002.

Chellappan, S. P., Hiebert, S., Mudryj, M., Horowitz, J. M. and Nevins J. R. (1991) *Cell*, 65, 1053–1061.

Chien, C. -T., Bartel, P. L., Sternglanz, R. and Fields, S. (1991) *Proc. Natl. Acad. Sci. USA*, 88, 9578–9582.

Courey, A. J. and Tjian, R. (1988). Cell 55, 887–898.

Dalton, S. (1992) *EMBO J.*, 11, 1797–1808.

Devoto, S. H., Mudryj, M., Pines, J., Hunter, T., and Nevins J. R. (1992) *Cell*, 68, 167–176.

Fields, S. and Song, O. (1989) *Nature*, 340, 245–246.

Girling, R., Partridge, J. F., Bandara, L. R., Burden, N., Totty, N. F., Hsuan, J. J. and La Thangue, N. B. (1993) *Nature*, 362, 83–87.

Guarente, L. and Mason, T. (1983) *Cell*, 32, 1279–1286.

Helin, K., Lees, J. A., Vidal, M., Dyson, N., Harlow, E. and Fattaey, A. (1992) *Cell*, 70, 337–350.

Hiebert, S. W., Chellappan, S. P., Horowitz, J. M., and Nevins J. R. (1992) *Genes and Development*, 6, 177–185.

Johnson, A. L., Barker, D. G. and Johnston, L. H. (1986) *Curr. Genet.*, 11, 107–112.

Kaelin, W. G., Krek, W., Sellers, W. R., DeCaprio, J. A., Ajchenbaum, F., Fuchs, C. H., Chittenden, T., Li, Y., Farnham, P. J., Blanar, M. A., Livingston, D. M. and Flemington, E. K. (1992) *Cell*, 70, 351–364.

La Thangue, N. B. and Rigby, P. W. J. (1987) *Cell*, 49, 507–513.

La Thangue, N. B., Thimmappaya, B. and Rigby, P. W. J. (1990) *Nucleic Acids Res.*, 18, 2929–2938.

La Thangue, N. B. and Taylor, W. (1993) *Trends Cell Biol.*, 3, 75–76.

Lees, E., Faha, B., Dulic, V., Reed, S. I. and Harlow, E. (1992) *Genes and Development*, 6, 1874–1885.

Means, A. L., Slansky, J. E., McMahon, S. L., Knuth, M. W. and Farnham, P. J. (1992) *Mol. Cell. Biol.*, 12, 1054–1063.

Mudryj, M., Devoto, S. H., Hiebert, S. W., Hunter, T., Pines, J. and Nevins J. R. (1991) *Cell*, 65, 1243–1253

Shirodkar, S., Ewen, M., DeCaprio, J. A., Morgan, J., Livingston, D. M. and Chittenden, T. (1992) *Cell*, 68, 157–166

Shivji, M. K., and La Thangue, N. B. (1991) *Mol. Cell. Biol.*, 11, 1686–1695

Webster, N. J. G., Green, S., Tasset, D., Ponglikitmongkol, M. and Chambon, P. (1989). *EMBO J.*, 8, 1444–1446.

Zamanian, M. and La Thangue, N. B. (1992) *EMBO J.*, 11, 2603–2610.

Zamanian, M. and La Thangue, N. B. (1993) *Mol. Biol. Cell.*, 4, 389–396

The invention claimed is:

1. A screening method for identifying putative chemotherapeutic agents which comprises:
providing a DRTF1 transcription factor, said transcription factor being a heterodimeric complex of a first component and a second component, the first component being selected from the group consisting of (i) the protein of SEQ ID NO: 2; or (ii) a polypeptide comprising amino acids identical to amino acids 160–220 of SEQ ID NO: 2; and the second component being E2F-1 or an E2F-1 family member having at least 70% homology to E2F-1 over the DNA binding region;
providing a putative chemotherapeutic agent; and
determining the extent to which said agent is capable of disrupting or inhibiting the formation or activity of said heterodimeric complex whereby the agent is identified as a putative chemotherapeutic agent if it shows ability to disrupt or inhibit the formation or activity of said complex.

2. An assay according to claim 1 wherein the activity of the heterodimeric complex is measured by its ability to bind an E2F-1 DNA binding site in vitro.

3. An assay according to claim 1 wherein the activity of the heterodimeric complex is measured by its ability to activate in vivo a promoter comprising an E2F-1 binding site linked to a reporter gene.

4. An assay according to claim 3 wherein the assay is performed in a yeast cell, insect cell or a mammalian cell.

5. An assay according to claim 1 wherein the first component is the protein of SEQ ID NO: 2.

6. An assay according to claim 1 wherein the first component comprises amino acid residues 59 to 410 of SEQ ID NO: 2.

7. An assay according to claim 1 wherein the first component comprises amino acid residues 84 to 249 of the SEQ ID NO: 1.

8. An assay according to claim 1 wherein the first component comprises amino acid residues 84 to 204 of the SEQ ID NO: 2.

9. An assay according to claim 1 wherein the first component comprises amino acid residues 146 to 249 of the SEQ ID NO: 2.

10. An assay according to claim 1 wherein the first component comprises amino acid residues 146 to 204 of the SEQ ID NO: 2.

11. An assay according to claim 1 wherein the second component is in the form of a fusion protein.

12. An assay according to claim 11 wherein the fusion protein is a GST fusion protein.

13. An assay according to claim 1 wherein one or more components carry a radioactive or colorimetric or fluorescent label.

14. A method of identifying a compound which disrupts complex formation or activity of a DRTF1 transcription factor, said method comprising:

providing a first component selected from the group consisting of (i) the protein of SEQ ID NO: 2; and (ii) a polypeptide having at least 70% homology over at least 20 contiguous amino acids to SEQ ID NO: 2;

providing a second component selected from the group consisting of E2F-1 and an E2F-1 family member having at least 70% homology to E2F-1 over the DNA binding region;

providing said compound; and determining the extent to which said compound is capable of disrupting or inhibiting the formation or activity of a heterodimeric complex formed of said first component and said second component.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 1700 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 55..1284

(xi) SEQUENCE DESCRIPTION: SEQ ID NO: 1:

```
GTTTCTTCTG TGGAGGGTAC GCAGTTAAAG CCTTGATTTC CTGGATCTGG TAAC ATG        57
                                                            Met
                                                              1

GCA AAA GAT GCC AGT CTA ATT GAA GCC AAC GGA GAA CTA AAG GTC TTT       105
Ala Lys Asp Ala Ser Leu Ile Glu Ala Asn Gly Glu Leu Lys Val Phe
            5                  10                  15

ATA GAC CAG AAT CTT AGT CCT GGG AAA GGT GTG GTA TCT CTT GTA GCC       153
Ile Asp Gln Asn Leu Ser Pro Gly Lys Gly Val Val Ser Leu Val Ala
         20                  25                  30

GTC CAC CCG TCC ACA GTC AAC ACA CTT GGG AAG CAG CTT TTG CCA AAA       201
Val His Pro Ser Thr Val Asn Thr Leu Gly Lys Gln Leu Leu Pro Lys
 35                  40                  45

ACC TTC GGA CAG TCC AAT GTC AAT ATC ACA CAG CAA GTG GTG ATT GGC       249
Thr Phe Gly Gln Ser Asn Val Asn Ile Thr Gln Gln Val Val Ile Gly
 50                  55                  60                  65

ACG CCT CAG AGA CCG GCA GCA TCC AAC ACT ATT GTG GTA GGA AGC CCA       297
Thr Pro Gln Arg Pro Ala Ala Ser Asn Thr Ile Val Val Gly Ser Pro
             70                  75                  80

CAC ACT CCC AAC ACG CAT TTT GTG TCA CAG AAC CAG ACG TCT GAC TCC       345
His Thr Pro Asn Thr His Phe Val Ser Gln Asn Gln Thr Ser Asp Ser
         85                  90                  95

TCA CCT TGG TCT GCT GGG AAG CGG AAC AGG AAG GGC GAG AAG AAT GGC       393
Ser Pro Trp Ser Ala Gly Lys Arg Asn Arg Lys Gly Glu Lys Asn Gly
    100                 105                 110

AAG GGC CTG CGG CAT TTC TCC ATG AAG GTG TGT GAG AAG GTG CAG AGG       441
Lys Gly Leu Arg His Phe Ser Met Lys Val Cys Glu Lys Val Gln Arg
115                 120                 125

AAA GGA ACC ACC TCC TAC AAT GAG GTG GCT GAC GAG CTG GTG GCA GAG       489
Lys Gly Thr Thr Ser Tyr Asn Glu Val Ala Asp Glu Leu Val Ala Glu
130                 135                 140                 145

TTC AGC GCT GCC GAC AAC CAC ATT CTA CCA AAC GAA TCA GCT TAT GAC       537
Phe Ser Ala Ala Asp Asn His Ile Leu Pro Asn Glu Ser Ala Tyr Asp
                150                 155                 160

CAG AAG AAC ATC CGG CGG CGT GTC TAC GAT GCC TTA AAT GTG CTA ATG       585
Gln Lys Asn Ile Arg Arg Arg Val Tyr Asp Ala Leu Asn Val Leu Met
            165                 170                 175

GCC ATG AAC ATC ATC TCC AAG GAG AAG AAG GAG ATC AAA TGG ATC GGC       633
Ala Met Asn Ile Ile Ser Lys Glu Lys Lys Glu Ile Lys Trp Ile Gly
        180                 185                 190

CTG CCC ACC AAC TCA GCT CAG GAG TGC CAG AAC TTA GAG GTG GAG AGG       681
Leu Pro Thr Asn Ser Ala Gln Glu Cys Gln Asn Leu Glu Val Glu Arg
    195                 200                 205
```

-continued

```
CAG AGG AGG CTG GAG AGG ATC AAA CAG AAG CAG TCT CAG CTC CAG GAG        729
Gln Arg Arg Leu Glu Arg Ile Lys Gln Lys Gln Ser Gln Leu Gln Glu
210                 215                 220                 225

CTC ATC CTG CAG CAA ATT GCC TTC AAG AAC TTG GTG CAG AGA AAT CGC        777
Leu Ile Leu Gln Gln Ile Ala Phe Lys Asn Leu Val Gln Arg Asn Arg
                230                 235                 240

CAA GCT GAG CAG CAG GCC CGC AGG CCG CCT CCT CCC AAC TCT GTC ATC        825
Gln Ala Glu Gln Gln Ala Arg Arg Pro Pro Pro Pro Asn Ser Val Ile
            245                 250                 255

CAC TTG CCC TTC ATC ATT GTC AAC ACC AGC AGG AAG ACA GTC ATT GAC        873
His Leu Pro Phe Ile Ile Val Asn Thr Ser Arg Lys Thr Val Ile Asp
        260                 265                 270

TGC AGC ATC TCC AAT GAC AAA TTT GAG TAT CTG TTT AAC TTT GAC AAC        921
Cys Ser Ile Ser Asn Asp Lys Phe Glu Tyr Leu Phe Asn Phe Asp Asn
275                 280                 285

ACG TTT GAG ATC CAC GAT GAC ATT GAG GTG CTC AAG CGC ATG GGC ATG        969
Thr Phe Glu Ile His Asp Asp Ile Glu Val Leu Lys Arg Met Gly Met
290                 295                 300                 305

GCA TGT GGG CTG GAG TCT GGC AAC TGC TCT GCT GAA GAC CTC AAG GTG       1017
Ala Cys Gly Leu Glu Ser Gly Asn Cys Ser Ala Glu Asp Leu Lys Val
                310                 315                 320

GCC AGA AGT TTG GTA CCA AAA GCT CTA GAA CCA TAC GTG ACA GAA ATG       1065
Ala Arg Ser Leu Val Pro Lys Ala Leu Glu Pro Tyr Val Thr Glu Met
            325                 330                 335

GCT CAG GGA TCC ATT GGT GGC GTA TTC GTC ACG ACA ACA GGT TCT ACA       1113
Ala Gln Gly Ser Ile Gly Gly Val Phe Val Thr Thr Thr Gly Ser Thr
        340                 345                 350

TCC AAT GGC ACA AGG CTT TCT GCC AGT GAT TTG AGC AAT GGT GCA GAT       1161
Ser Asn Gly Thr Arg Leu Ser Ala Ser Asp Leu Ser Asn Gly Ala Asp
355                 360                 365

GGG ATG CTG GCC ACG AGC TCC AAT GGG TCT CAG TAC AGC GGC TCC AGG       1209
Gly Met Leu Ala Thr Ser Ser Asn Gly Ser Gln Tyr Ser Gly Ser Arg
370                 375                 380                 385

GTC GAG ACC CCT GTG TCC TAC GTT GGG GAG GAT GAT GAC GAT GAT          1257
Val Glu Thr Pro Val Ser Tyr Val Gly Glu Asp Asp Asp Asp Asp
                390                 395                 400

GAC TTT AAT GAG AAC GAC GAG GAG GAT TGATTACTCA ACCCGTAGAC             1304
Asp Phe Asn Glu Asn Asp Glu Glu Asp
                405                 410

CCCTCTCCCC TTCGAATCAG CTTCAGGAAA AACACGTATA GAGGAAAGAA ACTTAAAGTG   1364

GGGCTTTCTG TTCTTTTTGG CCTACTCCCA AGAAGATACC CGCGAGTTCT GGAGTTGAGT   1424

GTGCAGCTCC AAGTGAGGAG GAGTGTGCGC AGTTTGAGCC TAGCTGCGGA TGTGTTGTGA   1484

AGCCAGCGTG CTAATGCAGA GCCTCTATCT ACCTTTTAGG ATTTTATGGT TTCTCTCTTT   1544

TCTCTCTTTT TTTTCCTTTT CTTTCTTTTT TGAGTTTGAA GCTTATTTTG CCCCTCAACA   1604

GTTGTTGCTG GGTTTGCCGA GGAAACTGTA CTGCGCCCAC ACCAGTGACA ATGACAAAGT   1664

GCTGCCCTGC CTCCGATGTC CAGCACCCAG GTGGTG                            1700
```

(2) INFORMATION FOR SEQ ID NO: 2:

(i) SEQUENCE CHARACTERISTICS:
        (A) LENGTH: 410 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Lys Asp Ala Ser Leu Ile Glu Ala Asn Gly Glu Leu Lys Val
  1               5                  10                  15
Phe Ile Asp Gln Asn Leu Ser Pro Gly Lys Gly Val Val Ser Leu Val
             20                  25                  30
Ala Val His Pro Ser Thr Val Asn Thr Leu Gly Lys Gln Leu Leu Pro
         35                  40                  45
Lys Thr Phe Gly Gln Ser Asn Val Asn Ile Thr Gln Gln Val Val Ile
 50                  55                  60
Gly Thr Pro Gln Arg Pro Ala Ala Ser Asn Thr Ile Val Val Gly Ser
 65                  70                  75                  80
Pro His Thr Pro Asn Thr His Phe Val Ser Gln Asn Gln Thr Ser Asp
                 85                  90                  95
Ser Ser Pro Trp Ser Ala Gly Lys Arg Asn Arg Lys Gly Glu Lys Asn
             100                 105                 110
Gly Lys Gly Leu Arg His Phe Ser Met Lys Val Cys Glu Lys Val Gln
             115                 120                 125
Arg Lys Gly Thr Thr Ser Tyr Asn Glu Val Ala Asp Glu Leu Val Ala
         130                 135                 140
Glu Phe Ser Ala Ala Asp Asn His Ile Leu Pro Asn Glu Ser Ala Tyr
145                 150                 155                 160
Asp Gln Lys Asn Ile Arg Arg Val Tyr Asp Ala Leu Asn Val Leu
                 165                 170                 175
Met Ala Met Asn Ile Ile Ser Lys Glu Lys Glu Ile Lys Trp Ile
             180                 185                 190
Gly Leu Pro Thr Asn Ser Ala Gln Glu Cys Gln Asn Leu Glu Val Glu
             195                 200                 205
Arg Gln Arg Arg Leu Glu Arg Ile Lys Gln Lys Gln Ser Gln Leu Gln
     210                 215                 220
Glu Leu Ile Leu Gln Gln Ile Ala Phe Lys Asn Leu Val Gln Arg Asn
225                 230                 235                 240
Arg Gln Ala Glu Gln Gln Ala Arg Arg Pro Pro Pro Asn Ser Val
                 245                 250                 255
Ile His Leu Pro Phe Ile Ile Val Asn Thr Ser Arg Lys Thr Val Ile
             260                 265                 270
Asp Cys Ser Ile Ser Asn Asp Lys Phe Glu Tyr Leu Phe Asn Phe Asp
             275                 280                 285
Asn Thr Phe Glu Ile His Asp Asp Ile Glu Val Leu Lys Arg Met Gly
         290                 295                 300
Met Ala Cys Gly Leu Glu Ser Gly Asn Cys Ser Ala Glu Asp Leu Lys
305                 310                 315                 320
Val Ala Arg Ser Leu Val Pro Lys Ala Leu Glu Pro Tyr Val Thr Glu
                 325                 330                 335
Met Ala Gln Gly Ser Ile Gly Gly Val Phe Val Thr Thr Thr Gly Ser
             340                 345                 350
Thr Ser Asn Gly Thr Arg Leu Ser Ala Ser Asp Leu Ser Asn Gly Ala
         355                 360                 365
Asp Gly Met Leu Ala Thr Ser Ser Asn Gly Ser Gln Tyr Ser Gly Ser
     370                 375                 380
Arg Val Glu Thr Pro Val Ser Tyr Val Gly Glu Asp Asp Asp Asp
385                 390                 395                 400
Asp Asp Phe Asn Glu Asn Asp Glu Glu Asp
                 405                 410
```

(2) INFORMATION FOR SEQ ID NO: 3:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Pro Asn Thr His Phe Val
1               5

(2) INFORMATION FOR SEQ ID NO: 4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

CGCGGATCCC CNAAYACNCA YTTYGT                                  26

(2) INFORMATION FOR SEQ ID NO: 5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Ala Gln Glu Ser Gln Asn
1               5

(2) INFORMATION FOR SEQ ID NO: 6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (xi) SEQUENCE DESCRIPTION: SEQ ID NO: 6:

CGCGGATCCA RRTTYTGNBW YTCYTGNGC                               29

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 7:

TAGTTTTGCG GCTTAAATTT GA                                      22

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 8:

TAGTTTTCGA TATTAAATTT GA                              22

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 9:

TAGTTTTCTC GCTTAAATTT GA                              22

(2) INFORMATION FOR SEQ ID NO: 10:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 10:

TAGTTTTAGC GCTTAAATTT GA                              22

(2) INFORMATION FOR SEQ ID NO: 11:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:

```
Tyr Asp Gln Lys Asn Ile Arg Arg Arg Val Tyr Asp Ala Leu Asn Val
 1               5                  10                  15

Leu Met Ala Met Asn Ile Ile Ser Lys Glu Lys Lys Glu Ile Lys Trp
                20                  25                  30

Ile Gly Leu Pro Thr Asn Ser Ala Gln Gln Arg Arg Leu Glu Arg Ile
            35                  40                  45

Lys Gln Lys Gln Ser Gln Leu Gln Glu Leu Ile Leu Gln Gln Ile Ala
        50                  55                  60

Phe Lys Asn Leu Val Gln Arg Asn
 65                  70
```

(2) INFORMATION FOR SEQ ID NO: 12:

(i) SEQUENCE CHARACTERISTICS:
        (A) LENGTH: 73 amino acids
        (B) TYPE: amino acid
        (C) STRANDEDNESS: single

```
            (D) TOPOLOGY: linear (ii) MOLECULE TYPE: protein (xi) SEQUENCE DESCRIPTION: SEQ ID NO: 12:

Glu Val Leu Lys Val Gln Lys Arg Arg Ile Tyr Asp Ile Thr Asn Val
1               5                   10                  15

Leu Glu Gly Ile Gln Leu Ile Ala Lys Lys Ser Lys Asn His Ile Gln
                20                  25                  30

Trp Leu Gly Ser His Thr Thr Val Gly Val Gly Gly Arg Leu Glu Gly
                35                  40                  45

Leu Thr Gln Asp Leu Arg Gln Leu Gln Glu Ser Glu Gln Gln Leu Asp
    50                  55                  60

His Leu Met Asn Ile Cys Thr Thr Gln
65                      70

(2) INFORMATION FOR SEQ ID NO: 13:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 13:

Arg Arg Val Tyr Asp Ala Leu Asn Val Leu Met Ala Met Asn Ile Ile
1               5                   10                  15

Ser (2) INFORMATION FOR SEQ ID NO: 14:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 14:

Arg Arg Ile Tyr Asp Ile Thr Asn Val Leu Glu Gly Ile Gln Leu Ile
1               5                   10                  15

Ala
```